(12) United States Patent
Carlson et al.

(10) Patent No.: US 8,673,584 B2
(45) Date of Patent: Mar. 18, 2014

(54) INHIBITOR SCAFFOLD FOR THE INHIBITION OF THE ENZYME PHOSPHOENOLPYRUVATE CARBOXYKINASE

(71) Applicants: University of Kansas, Lawrence, KS (US); Florida Memorial University, Miami Gardens, FL (US)

(72) Inventors: Gerald Carlson, Kansas City, KS (US); Todd Holyoak, Wallenstein (CA); Sarah Sullivan, Wallenstein (CA); Rose Mary Stiffin, Miami Gardens, FL (US)

(73) Assignees: University of Kansas, Lawrence, KS (US); Florida Memorial University, Miami Gardens, FL (US)

( * ) Notice: Subject to any disclaimer, the term of this patent is extended or adjusted under 35 U.S.C. 154(b) by 0 days.

(21) Appl. No.: 13/675,198

(22) Filed: Nov. 13, 2012

(65) Prior Publication Data
US 2013/0109031 A1  May 2, 2013

Related U.S. Application Data

(60) Division of application No. 12/834,609, filed on Jul. 12, 2010, now abandoned, which is a continuation-in-part of application No. PCT/US2009/030761, filed on Jan. 12, 2009.

(60) Provisional application No. 61/020,570, filed on Jan. 11, 2008.

(51) Int. Cl.
*G01N 33/53* (2006.01)

(52) U.S. Cl.
USPC .......................................................... 435/7.8

(58) Field of Classification Search
USPC ........................................................... 435/7.8
See application file for complete search history.

(56) References Cited

U.S. PATENT DOCUMENTS

2007/0224301 A1  9/2007  Ribnicky et al. ............... 424/740

OTHER PUBLICATIONS

Anderson, Chemistry & Biology, vol. 10, 787-797, Sep. 2003.*
Sullivan et al. Biochemistry 2007, 46, 10078-10088.*
DeMarco et al. "Identification of S-Carboxymethyl-Thiopyruvate as the Product of OxidativeDeamination of S-Carboxymethyl-Cysteine" Molecular & Cellular Biochemistry 1974 3(1):3-7.
Meese et al. "Syntheses of Metabolites of S-Carboxymethl-L-Cysteine and S-Methyl-L-Cysteine and of Some Isotopically Labelled ($^2$H, $^{13}$C) Analogues" Archives of Pharmacal Research 1990 323:957-965.
Plazek, E. and Sucharda, E. "A Synthesis of Alpha-thiopyrindigo" Berichte der Deutshcen Chemischen Gesellschaft 1926 59B(368):2282-2284.
Sheehan, J.T. and Leitner, G.J. "Thieno[3, 2-b] pyridine. I. The Preparation and Properties of an S-Isosteric 8-Hydroxyquinoline" Journal of the American Chemical Society 1952 74:5501-5503.
Tomisawa et al. "Purification and Characterization of 3-Mercaptopyruvic Acid S-Conjugate Reductases" Biochemical Pharmacology 1990 40(9):2047-2057.
International Preliminary Report from PCT/US2009/030761, Jul. 13, 2010.
Anderson, A. C. "The Process of Structure-Based Drug Design" Chemistry & Biology 2003 10:787-797.
Ash et al. "Mammalian and Avian Liver Phosphoenolpryruvate Carboxykinase" The Journal of Biological Chemistry 1990 265(13):7377-7384.
Carlson et al. "A Vicinal Dithiol Containing an Essential Cysteine in Phosphoenolpyruvate Carboxykinase (guanosine triphosphate) from Cytosol of Rat Liver" Biochemistry 1978 17(250:5329-5338.
Cotelesage et al. "Crystal structure of *Anacrobiospirillum succiniciproducens* PEP Carboxykinase Reveals an Important Active Site Loop" The International Journal of Biochemistry & Cell Biology 2005 37:1829-1837.
Duffy, T. H. and Nowak, T. "H and P Relaxation Rate Studies of the Interaction of Phosphoenolpyruvate and Its Analogues with Avian Phosphoenolpyruvate Carboxykinase" Biochemistry 1985 24:1152-1160.
Dunten et al. "Crystal Structure of Human Cytosolic Phosphoenolpyruvate Carboxykinase Reveals a New GTP-Binding Site" Journal of Molecular Biology 2002 316:257-264.
Fitch et al. "Phosphocreatine Does Not Inhibit Rabbit Muscle Phosphofructokinase or Pyruvate Kinase" The Journal of Biological Chemistry 1979 254(22):11357-11359.
Guidinger P. F. and Nowak T. "Analogs of Oxalacetate as Potential Substrates for Phosphoenolpyruvate Carboxykinase" Archives of Biochemistry and Biophysics 1990 278(1):131-141.
Hebda C. A. and Nowak T. "The Purification, Characterization, and Activation of Phosphoenolpyruvate Carboxykinase from Chicken Liver Mitochondria" The Journal of Biological Chemistry 1982 257(10):5503-5514.
Hebda C. A. and Nowak T. "Phosphoenolpyruvate Carboxykinase" The Journal of Biological Chemistry 1982 257(10):5515-5522.
Holyoak et al. "Structural Insights into the Mechanism of PEPCK Catalysis" Biochemistry 2006 45:8254-8263.

(Continued)

*Primary Examiner* — Nizal Chandrakumar
(74) *Attorney, Agent, or Firm* — Licata & Tyrrell P.C.

(57) ABSTRACT

A PEPCK inhibitor can include identifying a molecule that has a size capable of fitting into and interacting with the PEPCK binding site and at least one of the following: (a) a first terminal substituent having co-planar atoms acting as metal ligands to the active site metal ion PEPCK; (b) at least one of an atom or substituent at positions 2 or 3 from the first terminal substituent includes a neutral carbon center or include an oxygen, sulfur, selenium, or other atom with similar physiochemical properties; (c) at least one of an atom or substituent at positions 2 or 3 from the first terminal substituent is devoid of an electropositive atom or substituents; or (d) a second terminal substituent opposite of the first terminal substituent, said second terminal substituent having an atom that is a hydrogen boding acceptor and/or is negatively charged.

1 Claim, 8 Drawing Sheets

(56) References Cited

OTHER PUBLICATIONS

Izui et al. "Phosphoenopyruvate Carboxylase of *Escherichia coli*. Inhibition by Various Analogs and Homologs of Phosphoenolpyruvate" Journal of Biochemistry 1983 94:1789-1795.

Janc J. W. et al. "A Kinetic Investigation of Phosphoenolpyruvate Carboxylase from *Zea mays*" Biochemistry 1992 31:6421-6426.

Janc J. W. et al. "Mechanistic Studies of Phosphoenolpyruvate Carboxylase from *Zea mays* Utilizing Formate as an Alternate Substrate for Bicarbonate" Biochemistry 1992 31:6441-6446.

Meyer C. R. et al. "A Kinetic Study of Phosphate and Organic Phosphates on the Activity of Phosphoenolpyruvate Carboxylase from *Crassula argentea*" Archives of Biochemistry and Biophysics 1989 271(1.):84-97.

Stiffin et al., "Differential Inhibition of Cystosolic PEPCK by Substrate Analogues. Kinetic and Structural Characterization of Inhibitor Recognition" Biochemistry 2008 47(7):2099-2109.

Stubbe J. and Kenyon G. L. "Analogs of Phosphoenolpyruvate. Substrate Specificities of Enolase and Pyruvate Kinase from Rabbit Muscle" Biochemistry 1972 11:338-345.

Sullivan S. M. and Holyoak T. "Structure of Rat Cytosolic PEPCK: Insight into the Mechanism of Phosphorylation and Decarboxylation of Oxaloacetic Acid" Biochemistry 2007 46:10078-10088.

Wormhoudt L. W. et al. "Disposition of 1,2-[$^{14}$C]Dibromoethane in Male Wistar Rats" Drug Metabolism and Disposition 1998 26(5):437-447.

International Search Report from PCT/US2009/030761, Aug. 11, 2009.

* cited by examiner

US 8,673,584 B2

INHIBITOR SCAFFOLD FOR THE INHIBITION OF THE ENZYME PHOSPHOENOLPYRUVATE CARBOXYKINASE

INTRODUCTION

This patent application is a divisional of U.S. patent application Ser. No. 12/834,609 filed Jul. 12, 2010, which is a continuation-in-part of PCT application PCT/US2009/030761, filed Jan. 12, 2009 which claims benefit of U.S. Patent Application Ser. No. 61/020,570, filed Jan. 11, 2008, which applications are incorporated herein by specific reference in their entirety.

This invention was made with government support under Grant Numbers NSF DMB 85-20311 awarded by the National Science Foundation. The government has certain rights in the invention.

BACKGROUND

Phosphoenolpyruvate carboxykinase ("PEPCK") is an enzyme used in the natural process of gluconeogenesis. It converts oxaloacetate into phosphoenolpyruvate and carbon dioxide. Whereas most reactions of gluconeogenesis can use the glycolysis enzymes in the opposite direction, the pyruvate kinase enzyme is irreversible. Therefore, the enzymes pyruvate carboxylase and phosphoenolpyruvate carboxykinase are used to provide an alternate path for effectively reversing its actions. The enzyme, PEPCK, interacts with oxaloacetate (OAA) and phosphoenolpyruvate (PEP).

In humans there are two isoforms of PEPCK; a cytosolic form cPEPCK (SwissProt P35558) and a mitochondrial isoform mPEPCK (SwissProt Q16822) which have 63.4% sequence identity, which are products of different genes (Beale, E. G., Chrapkiewicz, N. B., Scoble, H. A., Metz, R. J., Quick, D. P., Noble, R. L., Donelson, J. E., Biemann, K., and Granner, D. K. (1985) Rat hepatic cytosolic phosphoenolpyruvate carboxykinase (GTP). Structures of the protein, messenger RNA, and gene. *J Biol Chem* 260, 10748-10760; Utter, M. F., and Kolenbrander, H. M. (1972) in *The Enzymes* (Boyer, P. D., Ed.) pp 117-168, Academic Press, New York; Weldon, S. L., Rando, A., Matathias, A. S., Hod, Y., Kalonick, P. A., Savon, S., Cook, J. S., and Hanson, R. W. (1990) Mitochondrial phosphoenolpyruvate carboxykinase from the chicken. Comparison of the cDNA and protein sequences with the cytosolic isozyme. *J Biol Chem* 265, 7308-7317). Both forms bind free divalent metal cations, in addition to the metal-nucleotide complex. Although these isozymes share 63% identity and posses a virtually identical three-dimensional structure (Dunten, P., Belunis, C., Crowther, R., Hollfelder, K., Kammlott, U., Levin, W., Michel, H., Ramsey, G. B., Swain, A., Weber, D., and Wertheimer, S. J. (2002) Crystal structure of human cytosolic phosphoenolpyruvate carboxykinase reveals a new GTP-binding site. *J Mol Biol* 316, 257-264; Holyoak, T., Sullivan, S. M.; and Nowak, T. (2006) Structural Insights into the Mechanism of PEPCK Catalysis. *Biochemistry* 45, 8254-8263; Sullivan, S. M., and Holyoak, T. (2007) Structures of rat cytosolic PEPCK: Insight into the mechanism of phosphorylation and decarboxylation of oxaloacetic acid. *Biochemistry* 46, 10078-10088), they are immunologically distinct. It is almost certainly the cytosolic form which is important in gluconeogenesis, as there is no known transport mechanism to move PEP from the mitochondrion to the cytosol, where it is needed for gluconeogenesis.

As PEPCK acts at the junction between glycolysis and the Krebs cycle, it causes decarboxylation of a C4 molecule, creating a C3 molecule. As the first committed step in gluconeogenesis, PEPCK decarboxylates and phosphorylates OAA for its conversion to PEP, when GTP is present. As a phosphate is transferred, the reaction results in a GDP molecule.

PEPCK is enhanced, both in terms of its production and activation, by many factors. Transcription of the PEPCK gene is stimulated by glucagon, glucocorticoids, retinoic acid, and adenosine 3',5'-monophosphate (cAMP), while it is inhibited by insulin. Of these factors, insulin, a hormone that is deficient in the case of diabetes, is considered dominant, as it inhibits the transcription of many of the stimulatory elements. PEPCK activity is also inhibited by hydrazine sulfate, and the inhibition therefore decreases the rate of gluconeogenesis. Also, the use of siRNA to inhibit PEPCK in a diabetic mouse model shows elimination of the hyperglycemia upon PEPCK inhibition. Therefore, it would be advantageous to find novel inhibitors of PEPCK and/or an inhibitor scaffold for preparing analogs and derivatives thereof for novel inhibitors of PEPCK.

SUMMARY OF THE INVENTION

In one embodiment, the present invention can include a compound for inhibiting phosphoenolpyruvate carboxykinase (PEPCK) in a subject. Such a compound can include a molecular structure configured for interacting with a biding site of PEPCK so as to inhibit PEPCK. The PEPCK inhibitor can be characterized by having a size capable of fitting into and interacting with the PEPCK binding site and at least one of the following: (a) a first terminal substituent having co-planar atoms acting as metal ligands to the active site metal ion PEPCK; (b) at least one of an atom or substituent at positions 2 or 3 from the first terminal substituent includes a neutral carbon center or include an oxygen, sulfur, selenium, or other atom with similar physiochemical properties; (c) at least one of an atom or substituent at positions 2 or 3 from the first terminal substituent is devoid of an electropositive atom or substituents; or (d) a second terminal substituent opposite of the first terminal substituent, said second terminal substituent having an atom that is a hydrogen boding acceptor and/or is negatively charged. For example, the PEPCK inhibitor can include at least one, two, three, or four of (a), (b), (c), or (d).

In one embodiment, the first terminal substituent can be characterized by any one or more of the following: at least one of the co-planar atoms of the first terminal substituent interacts with S286; the first terminal substituent has at least two cis-planar groups; the cis-planar groups are independently selected from carbonyls, amines, sulfhydryls, alcohols, or combinations thereof; the oxygen, nitrogen, or sulfur atoms of the cis-planar groups have an oxidation state; or at least one of the cis-planar groups is a carboxyl group that interacts with S286.

In one embodiment, at least one of the atoms or substituents at positions 2 or 3 from the first terminal substituent can be characterized by any one or more of the following: is electron rich atom or substituent so as to interact with at least one of R87 or R405 (e.g., shown in FIG. 4 for CMMP described below); is devoid of an electropositive atom or substituent that inhibits an interaction with one of R87 or R405; includes a carbonyl, carboxylate, ketone, or sulfonate moiety; interacts with R405 and/or R87 through an electrostatic interaction and/or hydrogen bonding (e.g., CMMP has this interaction); at least one of positions 2 or 3 from the first terminal substituent includes a neutral carbon center; or both positions 2 and 3 include a neutral carbon center.

In one embodiment, the second terminal substituent can be characterized by any one or more of the following: includes a hydrogen bonding acceptor so as to interact with Y235 and/or N403; includes a negative charge so as to interact with Y235 and/or N403; has an edge-on aromatic interaction with Y235; includes a carbonyl group; or is devoid of a positive charge.

In one embodiment, the distance between the first terminal substituent and the second terminal substituent is 5 backbone atoms or less. This can be any one of 5, 4, 3, or 2 atoms in order to fit within the PEPCK binding site.

In one embodiment, the PEPCK inhibitor is selected from the group consisting of 3-[(carboxycarbonyl)oxy]-3-oxopropanoic acid, 3-[(carboxycarbonyl)oxy]propanoic acid, 3-[(carboxymethyl)sulfanyl]-2-oxopropanoic acid, (5,6-dioxo-1,4-dioxan-2-yl)acetic acid, (5,6-dioxo-5,6-dihydro-1,4-dioxin-2-yl)acetic acid, (2-hydroxy-5,6-dioxo-1,4-dioxan-2-yl)acetic acid, salts thereof, acids thereof, derivatives thereof, or combinations thereof.

In one embodiment, the PEPCK inhibitor is or includes features of one of Formulas A, B, C, or D, or salt thereof, acid thereof, derivative thereof or combinations thereof so as to interact with M2+ active metal site of PEPCK through interactions (a) and (b) of the structures of Formula A, Formula B, Formula C, and Formula D shown below.

In one embodiment, the PEPCK inhibitor is devoid of being characterized by at least one of the following: a methyl or methylene center which is incapable of interacting with R405; a size incapable of fitting within the binding pocket framed by R87, K244, G237, F333, R405, N403 and/or Y235; a steric conflict with F333; or a positively charged functional group incompatible with a positively charged active site of PEPCK.

In one embodiment, the PEPCK inhibitor has a structure of Formula C, Formula E, or Formula G, or derivative or salt thereof.

In one embodiment, the present invention can include a pharmaceutical composition for inhibiting phosphoenolpyruvate carboxykinase (PEPCK) in a subject. Such a composition can include a pharmaceutically acceptable carrier; and a therapeutically effective amount of a PEPCK inhibitor as described herein. For example, the PEPCK inhibitor can be present in a therapeutically effective amount for treating, inhibiting, and/or hyperglycemia in the subject. The subject can be a diabetic patient or someone susceptible to becoming a diabetic patient.

In one embodiment, the present invention can include a method for designing a molecule capable of functioning as a PEPCK inhibitor. Such a method can include identifying a molecule having one or more features of a PEPCK inhibitor as described herein. This can include combining one or more features that are described to provide favorable interactions with PEPCK. Such a molecule can then be synthesized and tested for affinity and selectivity with PEPCK.

In one embodiment, the present invention can include a method for inhibiting phosphoenolpyruvate carboxykinase (PEPCK) in a subject. Such a method can include administering to the subject a composition having a PEPCK inhibitor as described herein. The PEPCK inhibitor can be administered in a therapeutically effective amount for treating, inhibiting, and/or hyperglycemia in the subject. The subject can be a diabetic patient.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 1A) PEPCK-$Mn^{2+}$-oxalate, FIG. 1B) PEPCK-$Mn^{2+}$-phosphonoformate, FIG. 1C) PEPCK-$Mn^{2+}$-PGA, FIG. 1D) PEPCK-$Mn^{2+}$-PGA, FIG. 1E) PEPCK-$Mn^{2+}$-phosphonopropionate, and FIG. 1F) PEPCK-$Mn^{2+}$ sulfoacetate complexes. The dashed lines indicate potential hydrogen bonds and metal-water interactions. In addition, a potential salt bridge between R405 and the sulfate of sulfoacetate is shown in FIG. 1F. All distances indicated in FIGS. 1A-1F are in Ångstroms. The $F_o$-$F_c$ density rendered at FIG. 1A) 2.7 σ, FIG. 1B) 3.3 σ, FIG. 1C) 2.4 σ, FIG. 1D) 2.4 σ, FIG. 1E) 3.1 σ, and FIG. 1F) 2.8 σ prior to the inclusion of the ligands into the model is shown as a blue mesh. The $F_o$-$F_c$ density shown in FIG. 1D is the residual $F_o$-$F_c$ density after refinement of the PGA conformation shown in FIG. 1C.

FIGS. 2A and 2B are merely a rotation of 6 degrees with respect to each other.

DETAILED DESCRIPTION OF THE INVENTION

Figure 1A:
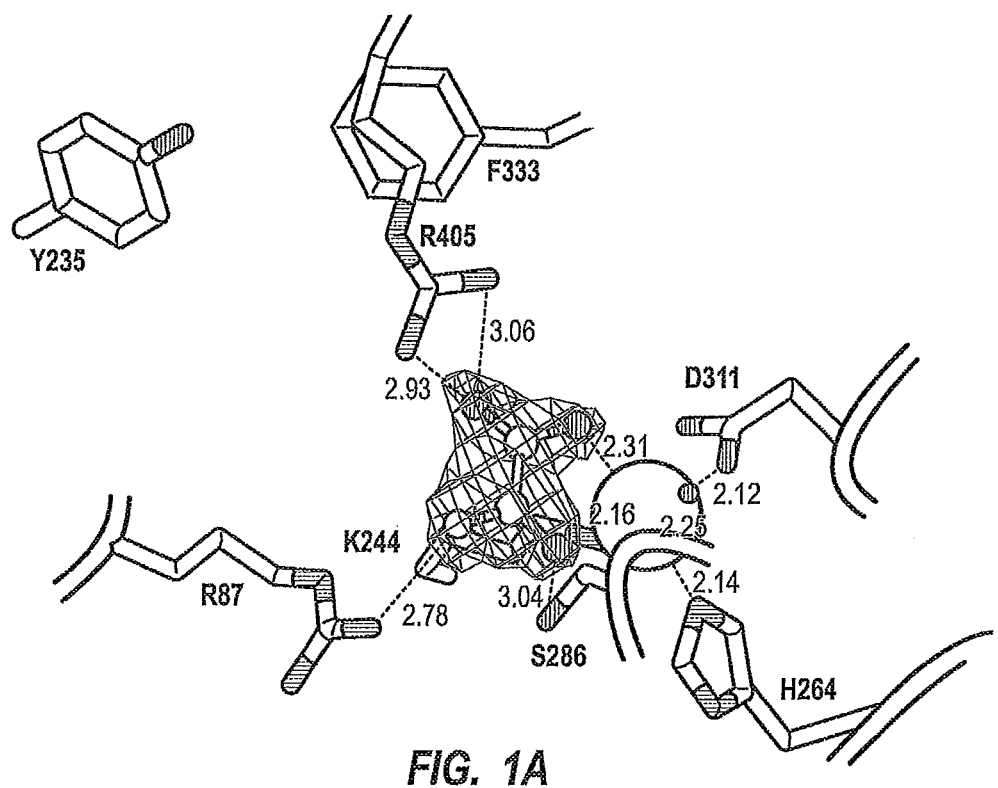
FIGS. 1A-1F schematically illustrate the modes of inhibitor binding to rat cPEPCK. Shown are.

Studies to delineate the topography of the active sites of the isozymes of PEPCK have been performed using analogues of PEP or OAA, either as reversible inhibitors or as alternative substrates (Ash, D. E., Emig, F. A., Chowdhury, S. A., Satoh, Y., and Schramm, V. L. (1990) Mammalian and Avian Liver Phosphoenolpyruvate Carboxykinase—Alternate Subs;

Guidinger, P. F., and Nowak, T. (1990) Analogs of oxalacetate as potential substrates for phosphoenolpyruvate carboxykinase. Arch Biochem Biophys 278, 131-141). Alkyl or halo derivatives of PEP at the third carbon, using the numbering system of Stubbe and Kenyon (Stubbe, J. A., and Kenyon, G. L. (1972) Analogs of phosphoenolpyruvate. Substrate specificities of enolase and pyruvate kinase from rabbit muscle. Biochemistry 11, 338-345) have demonstrated stereospecificity of the reaction catalyzed by mPEPCK from avian liver (Duffy, T. H., and Nowak, T. (1985) 1H and 31P relaxation rate studies of the interaction of phosphoenolpyruvate and its analogues with avian phosphoenolpyruvate carboxykinase. Biochemistry 24, 1152-1160). Also, α-hydroxyl and α-sulfhydryl carboxylic acids have been found to be poor substrates for PEPCK phosphoryl transfer reaction (Ash et al. 1990).

The present invention has provided systematic substrate analogues of PEP and OAA that are reversible inhibitors of PEPCK, which inhibition was assayed against PEP. With the exception of three compounds, the PEPCK inhibitors were bifunctional, being predominantly bicarboxylic acids, biphosphonic acids, or bisulfonic acids. Some of the bifunctional compounds are also phosphoryl or sulfonyl monocarboxylic acids. None is an amide, ester, or acyl halide because earlier studies have shown that such analogues are usually poor alternative substrates or inhibitors (Stubbe at al. 1972).

Although some of the analogues screened and described herein have been used previously to study the PEP/OAA binding site of PEP-dependent enzymes (Fitch, C. D., Chevli, R., and Jellinek, M. (1979) Phosphocreatine does not inhibit rabbit muscle phosphofructokinase or pyruvate kinase. J Biol Chem 254, 11357-11359; Izui, K., Matsuda, Y., Kameshita, I., Katsuki, H., and Woods, A. E. (1983) Phosphoenolpyruvate carboxylase of *Escherichia coli*. Inhibition by various analogs and homologs of phosphoenolpyruvate. J Biochem (Tokyo) 94, 1789-1795; Janc, J. W., Cleland, W. W., and O'Leary, M. H. (1992) Mechanistic studies of phosphoenolpyruvate carboxylase from *Zea mays* utilizing formate as an alternate substrate for bicarbonate. Biochemistry 31, 6441-6446; and, J. W., O'Leary, M. H., and Cleland, W. W. (1992) A kinetic investigation of phosphoenolpyruvate carboxylase from *Zea mays*. Biochemistry 31, 6421-6426; Meyer, C. R., Rustin, P., and Wedding, R. T. (1989) A kinetic study of the effects of phosphate and organic phosphates on the activity of phosphoenolpyruvate carboxylase from *Crassula argentea*. Arch Biochem Biophys 271, 84-97), such as mPEPCK, few have been evaluated as substrate analogues of rat liver cPEPCK and none have been structurally characterized in complex with the GTP-dependent PEPCK isozyme. Many of the compounds, such as sulfoacetate, 2,2-dimethylsulfoaceate, methanediphosphonate, and 1,2-ethanediphosphonate, have not been previously evaluated as analogues of OAA or PEP or as inhibitors of PEPCK.

Some of the small molecule compounds utilized in the studies have been shown to inhibit PEPCK, however, they also inhibit a number of different enzymes as well (e.g., very little to no selectivity). For those compounds that have been demonstrated previously to inhibit PEPCK, their mechanism of interaction with PEPCK was previously unknown. Therefore, rationale design of new compounds based upon the interactions of these non-selective compounds was impossible prior to the structural and kinetic studies described herein. Also, the notion that there are two subsites within the same active site of PEPCK, one for PEP and one for OAA was unknown prior to the present studies. The data demonstrate that some of the molecules studied bind specifically to one or the other of the two possible subsites of PEPCK. This key observation allows new and unique compounds to be designed and synthesized so as to incorporate features of recognition of PEPCK suggested by the characterization. A PEPCK inhibitor can include one or more features of the individual compounds into one molecule.

Structural-function analysis of PEPCK illustrates that the ability of compounds having certain features to inhibit PEPCK, where such features can be dependent upon the overall size, orientation, electronic properties, and charge of the functional groups on the compounds. Structural characterizations of the compounds bound to PEPCK demonstrate that in general there are two distinct classes of competitive inhibitors for PEPCK. The first class includes compounds that mimic PEP binding to the enzyme in an outer-sphere geometry with respect to the active site metal, and have an order of magnitude lower affinity for PEPCK than the second class of compounds that mimic the binding of OAA, which has been found to directly coordinate to the active site metal ion. The novel structure-function analysis presented herein illustrates the mechanism of molecular recognition used by PEPCK for selective interaction, which can be exploited to develop novel and selective inhibitors of this important enzyme. Thus, the information obtained from the structural-function analysis can be used to design molecules that are selective inhibitors of PEPCK, and such selective molecules can be used for inhibiting PEPCK for therapeutic purposes.

The structure-function analysis identified novel mechanisms of molecular recognition of PEP and OAA by cPEPCK. As such, the systematic evaluation of a variety of PEP and OAA analogues determined the features of molecules that can function as potential reversible inhibitors of the enzyme against PEP. The molecules that inhibit PEPCK in a competitive fashion were found to fall into two general classes. Those molecules that can be competitive inhibitors of PEPCK that mimic the binding geometry of PEP, namely phosphoglycolate and 3-phosphonopropionate, are found to bind weakly (millimolar $K_i$ values). In contrast, those molecules that can be competitive inhibitors that mimic the binding geometry of OAA (oxalate and phosphonoformate) coordinate directly to the active site manganese ion, and bind an order of magnitude more tightly (micromolar $K_i$ values). Additionally, competitive inhibitor sulfoacetate is found to be an outlier of these two classes, and binds in a hybrid fashion utilizing modes of recognition of both PEP and OAA in order to achieve a micromolar inhibition constant in the absence of direct coordination to the active site metal. The kinetic studies in combination with the structural characterization of the five aforementioned competitive inhibitors demonstrates the molecular requirements for high affinity binding of molecules to the active site of PEPCK. Examples of these features include (1) cis-planar carbonyl groups for coordination to the active site metal, (2) a bridging electron rich atom at the position corresponding to the C2 methylene group of OAA to facilitate interactions with R405, (3) a carboxylate or sulfonate moiety at a position corresponding to the C1 carboxylate of OAA, and (4) an edge-on aromatic interaction between a carboxylate and Y235. Molecules can have one or more of the foregoing features in order to effectively inhibit PEPCK. Additional features of a PEPCK inhibitor are described below.

Each inhibitor of PEPCK is a new compound that can be included in a new composition of matter. The described inhibitors specifically and potently inhibit the enzyme PEPCK. The inhibitor inhibits the enzyme that is the rate limiting step in glucose synthesis. This will eliminate the production of glucose by the liver, and thereby eliminate the hyperglycemic condition in the peripheral tissues that leads to all the known diabetic complications including circulatory problems, including heart disease, and blindness. Thus, the PEPCK inhibitor can be used to: inhibit a hyperglycemic condition in the peripheral tissues; inhibit diabetic complications such as circulatory problems, including heart disease, and blindness; and thereby treat, inhibit, and/or prevent complications associated with diabetes.

In one embodiment, the inhibitor is designed to specifically inhibit the enzyme PEPCK over other enzymes, whose role in the metabolic production of glucose is well characterized. The PEPCK activity increases under conditions of hyperglycemia in diabetic patients, and thus inhibition of PEPCK can treat and/or inhibit hyperglycemia.

In one embodiment, the present invention can include a compound for inhibiting phosphoenolpyruvate carboxykinase (PEPCK) in a subject. Such a compound can include a molecular structure configured for interacting with a biding site of PEPCK so as to inhibit PEPCK.

The molecule can inhibit PEPCK so as to inhibit gluconeogenesis, which in many instances is the rate-limiting step. Gluconeogenesis is a major contributor to hyperglycemia in diabetics, not just impaired peripheral glucose uptake, and PEPCK is greatly elevated in diabetes. Accordingly, lowering PEPCK activity through inhibitors that interact with and inhibit the function of PEPCK can lead to lowered blood glucose. Lowered blood glucose is beneficial to treat and/or inhibit hyperglycemia.

The molecule for inhibiting PEPCK (i.e., PEPCK inhibitor) can be selected to include the features for interacting with PEPCK. As such, various PEPCK inhibitors fall under the present invention. Additionally, the present invention can include a molecule that acts as a scaffold to allow for chemical substitutions that provide functionalities to participate in as many interactions with PEPCK as possible. Thus, the PEPCK inhibitor can have various geometric and physicochemical properties as described herein.

Also, the PEPCK inhibitor can include additional groups condensed onto the structures described herein in order to minimize the charges and encourage membrane permeability.

Examples of chemical structure-function properties that may increase or decrease the PEPCK binding inhibitors are shown below in Table 1 with respect to Compounds 1-35. Any of the molecules shown to have beneficial properties can be prepared into analogues thereof so as to utilize the properties in the design of a PEPCK inhibitor.

In one embodiment, a PEPCK inhibitor can be designed and/or synthesized so as to have a favorable chemical structure that binds with PEPCK, wherein the favorable chemical structure is a structure identified herein from at least a portion of a molecule type selected from the group consisting of dicarboxylates, phosphonyl monocarboxylates, phosphoryl monocarboxylates, sulfonyl monocarboxylates, sulfinyl monocarboxylates, diphosphoryls, disulfonates, epoxy compounds, aromatic compounds, salts thereof, acids thereof, or combinations thereof. The molecules that fall under the above-referenced groups are shown in Table 1.

In one embodiment, a PEPCK inhibitor can include a PEPCK-associating portion of a molecule selected from the group consisting of maleate, fumarate, itaconate, sulfosuccinate, 3-phosphonopropionate, sulfoacetate, 2,2-dimethyl sulfoacetate, 3-sulfopropionate, methanediphosphonate, 1,2-ethanediphosphonate, methanedisulfonate, and the like.

In one embodiment, a PEPCK inhibitor is devoid of a portion chemical feature that inhibits an interaction with PEPCK. A molecule that has such a feature that inhibits an interaction with PEPCK can be selected from the group consisting of 1,2-cyclopentanedicarboxylate, 2-amino-5-phosphonovalerate, serine phosphate, threonine phosphate, cysteic acid, cysteine sulfinic acid, 1,2-ethanedisulfonate, phosphomycin, phenylphosphate, and p-nitrophenylphosphate.

The PEPCK inhibitor can be characterized by having a size capable of fitting into and interacting with the PEPCK binding site and at least one of the following: (a) a first terminal substituent having co-planar atoms acting as metal ligands to the active site metal ion PEPCK; (b) at least one of an atom or substituent at positions 2 or 3 from the first terminal substituent includes a neutral carbon center or include an oxygen, sulfur, selenium, or other atom with similar physiochemical properties; (c) at least one of an atom or substituent at positions 2 or 3 from the first terminal substituent is devoid of an electropositive atom or substituents; or (d) a second terminal substituent opposite of the first terminal substituent, said second terminal substituent having an atom that is a hydrogen boding acceptor and/or is negatively charged. For example, the PEPCK inhibitor can include at least one, two, three, or four of (a), (b), (c), or (d). The characterizations described in (a), (b), (c), or (d) can be made with respect to any one of Compounds 36-41, Formulas A-D, or based on a scaffold thereof (Compounds 1-35 are shown in Table 1 below).

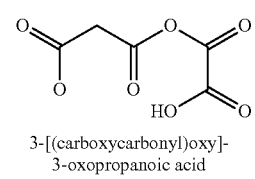

(Compound 36)

3-[(carboxycarbonyl)oxy]-
3-oxopropanoic acid

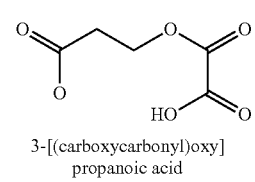

(Compound 37)

3-[(carboxycarbonyl)oxy]
propanoic acid

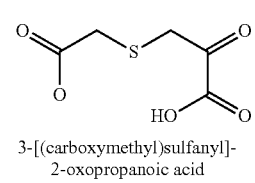

(Compound 38)

3-[(carboxymethyl)sulfanyl]-
2-oxopropanoic acid

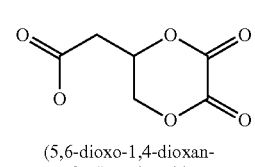

(Compound 39)

(5,6-dioxo-1,4-dioxan-
2-yl)acetic acid

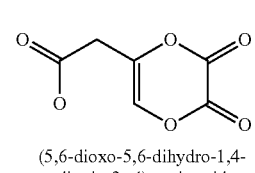

(Compound 40)

(5,6-dioxo-5,6-dihydro-1,4-
dioxin-2-yl)acetic acid (Compound 41)

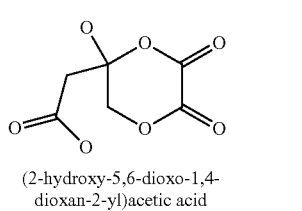

(2-hydroxy-5,6-dioxo-1,4-
dioxan-2-yl)acetic acid

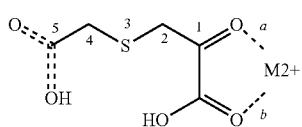

Formula A

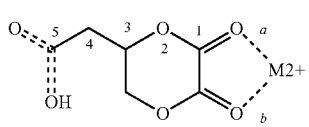

Formula B

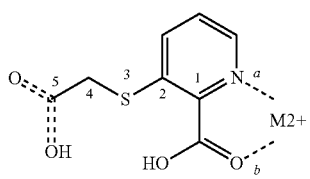

Formula C

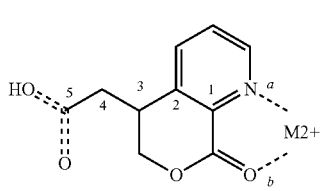

Formula D

As shown, the first terminal substituent, as shown on the right side of Formulas A-D include interactions a,b with the M2+ metal ligand of PEPCK. The second terminal substituent is shown in the left side of Formulas A-D.

According to Formulas A-D, the PEPCK inhibitors can have an overall geometry and/or stereoelectronic properties as shown in Formulas A-D and Compounds 36-41. M2+ represents the divalent cation bound at the PEPCK active site and the dashed lines (a,b) represent the metal coordination of the indicated atoms in the inhibitor to that same metal ion. A PEPCK inhibitor can have co-planar atoms (a,b) acting as metal ligands to the active site metal ion. The co-planar atoms could be oxygen, nitrogen, selenium or other similar atoms with similar physiochemical properties. The atom positions 2 and/or 3 as shown in the representative structures containing oxygen or sulfur can further include other electronegative atoms with similar physiochemical properties, and may be of any oxidation state. Also, atom positions 2 and/or 3 can contain neutral carbon centers. For example, one or both atom positions 2 and/or 3 can include atoms or substituents that are electronegative. Alternatively, one or both atom positions and/or 3 can be carbons. Also, the atom positions 2 and/or 3 should be devoid of atoms or substituents that are electropositive. A PEPCK inhibitor may combine any features of the three independent molecules shown in Formulas A-C (e.g., as shown in Formula D) as to facilitate as many favorable interactions between enzyme and inhibitor as possible to achieve optimal specificity and potency. The central backbone of the molecule scaffold (e.g., as shown in Formula A-D) can be limited to 5 atoms in length or equivalently as shown and constrained by the structural data defining the active site of PEPCK.

Figure 4:
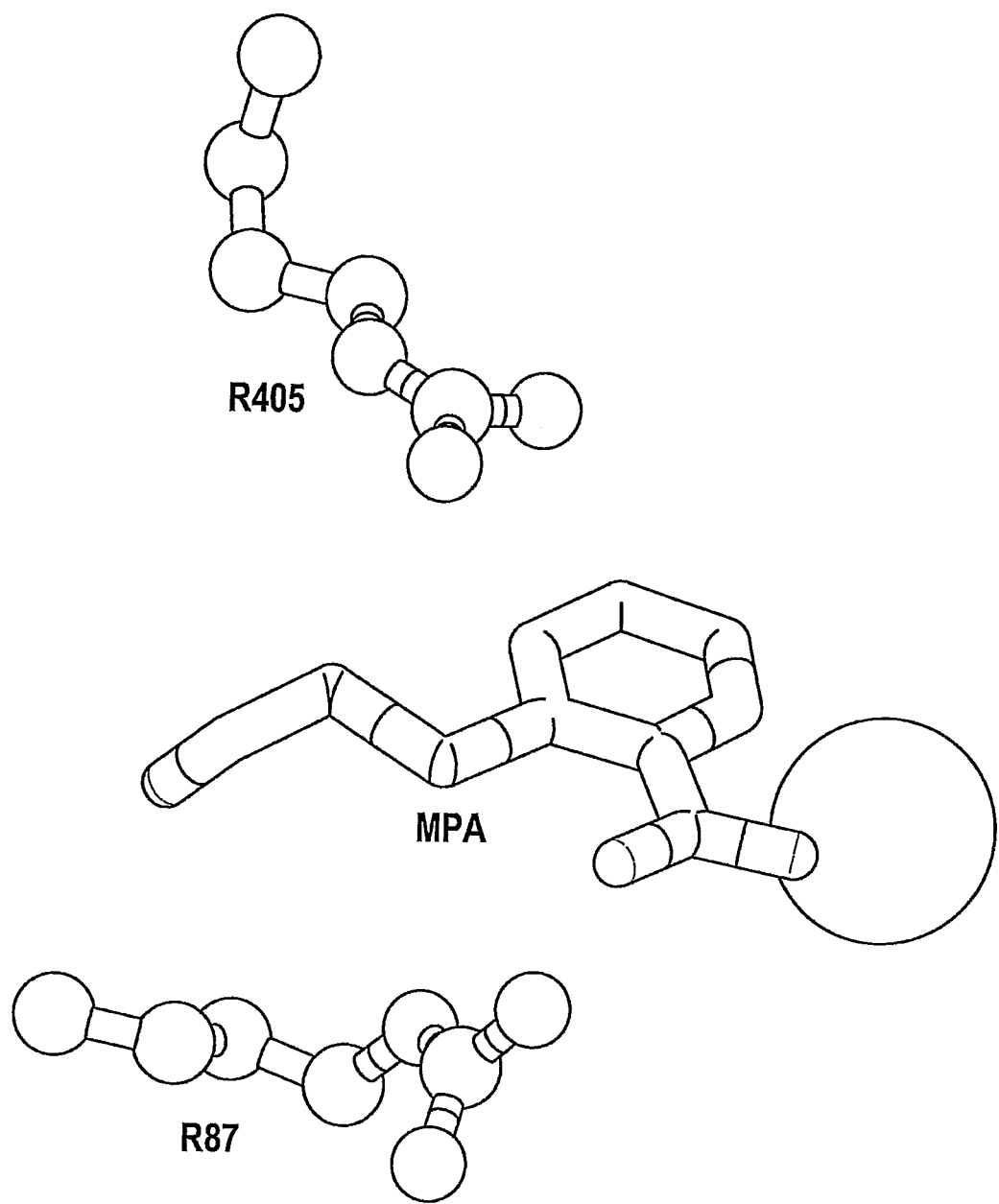
FIG. 4 is a schematic representation of a crystal structure of 3-carboxymethylmercaptopicolinic acid (3-(carboxymethylsulfanyl)pyridine-2-carboxylic acid; CMMP) bound to PEPCK bridging both OAA/PEP subsites.

In one embodiment, the PEPCK inhibitor can have a structure of Formula C or derivative thereof as shown in Formula E. The compound of Formula C is 3-carboxymethylmercaptopicolinic acid (3-(carboxymethylsulfanyl)pyridine-2-carboxylic acid; CMMP), which has now been identified as a PEPCK inhibitor as shown in the figures and described in the examples below. Based on the data for CMMP including FIGS. 4 and 5, it is conceived that derivatives of Formula C, which are shown in Formula E, may have similar PEPCK inhibitor functionality. Particularly, the crystallographic data in FIG. 4 provides evidence that the compounds of Formula E may have similar function to CMMP:

Formula E

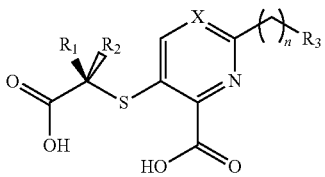

In Formula E: R1 can be a hydrogen, halogen, Cl, F, CH$_3$, CH$_3$CH$_2$, or higher or lower substituted or unsubstituted straight chain or branched aliphatic (e.g., C1-C10), where R1 is not electropositive (+ve) and can be electronegative (−ve), neutral, and/or an hydrogen bond donor; R2 can be hydrogen, CH$_3$CH$_2$, or higher or lower substituted or unsubstituted straight chain or branched aliphatic (e.g., C1-C10), and may be the same or different from R1; R3 can be a carboxylic acid, amide, Formula F, sulphate, phosphate, or other hydrogen bond donor or have a positive charge; X can be C, O, or N, such that X is an hydrogen bond donor; and n can be 0, 1, 2, or 3. Formula G shows another derivative of CMMP with R3 being carboxylic acid. Also, the sulfur atom can have an increased oxidation state other than the oxidation state shown. Alternatively, the sulfur group can be replaced by oxygen or nitrogen.

Formula F

Formula G

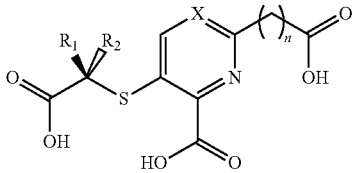

The PEPCK inhibitors of Formula C, E, and G include features that satisfy certain criteria for PEPCK inhibitor design as described herein. Accordingly, these PEPCK inhibitors can be characterized by having a size capable of fitting into and interacting with the PEPCK binding site and have following: (a) a first terminal substituent having co-planar atoms acting as metal ligands to the active site metal ion PEPCK (e.g., the nitrogen in the ring along with the carboxylic acid group linked to the ring); (b) at least one of an atom or substituent at positions 2 or 3 from the first terminal substituent includes a neutral carbon center or include an oxygen, sulfur, selenium, or other atom with similar physiochemical properties (e.g., the sulfur atom); (c) at least one of an atom or substituent at positions 2 or 3 from the first terminal substituent is devoid of an electropositive atom or substituents (e.g., sulfur atom or R1 and R1 substituents); or (d) a second terminal substituent opposite of the first terminal substituent, said second terminal substituent having an atom that is a hydrogen boding acceptor and/or is negatively charged (e.g., carboxylic acid group adjacent to R1 and R2).

In one embodiment, the first terminal substituent can be characterized by any one or more of the following: at least one of the co-planar atoms of the first terminal substituent interacts with S286; the first terminal substituent has at least two cis-planar groups; the cis-planar groups are independently selected from carbonyls, amines, sulfhydryls, alcohols, or combinations thereof; the oxygen, nitrogen, or sulfur atoms of the cis-planar groups have an oxidation state; or at least one of the cis-planar groups is a carboxyl group that interacts with S286.

In one embodiment, at least one of the atoms or substituents at positions 2 or 3 from the first terminal substituent can be characterized by any one or more of the following: is electron rich atom or substituent so as to interact with at least one of R87 or R405; is devoid of an electropositive atom or substituent that inhibits an interaction with one of R87 or R405; includes a carbonyl, carboxylate, ketone, or sulfonate moiety; interacts with R405 and/or R87 through an electrostatic interaction and/or hydrogen bonding; at least one of positions 2 or 3 from the first terminal substituent includes a neutral carbon center; or both positions 2 and 3 include a neutral carbon center.

In one embodiment, the second terminal substituent can be characterized by any one or more of the following: includes a hydrogen bonding acceptor so as to interact with Y235 and/or N403; includes a negative charge so as to interact with Y235 and/or N403; has an edge-on aromatic interaction with Y235; includes a carbonyl group; or is devoid of a positive charge.

In one embodiment, the distance between the first terminal substituent and the second terminal substituent is 5 backbone atoms or less. This can be any one of 5, 4, 3, or 2 atoms in order to fit within the PEPCK binding site.

For example, the PEPCK inhibitor can be characterized by at least one of the following: (1) the first terminal substituent includes at least two cis-planar groups capable of coordinating to an active site metal of PEPCK, examples are carbonyl groups, amines, sulfhydryl, alcohol or the like, and can have oxygen, nitrogen or sulfur atoms of some oxidation state; (2) a bridging electron rich atom at a position corresponding to a C2 methylene group of oxaloacetate to facilitate interactions with R405; (3) a carboxylate, ketone, carbonyl, sulfonate moiety or the like at a position corresponding to a C1 carboxylate of oxaloacetate; and (4) an edge-on aromatic interaction between the second terminal substituent and Y235, where the second terminal substituent is a carbonyl (e.g., carboxylate).

In another example, the PEPCK inhibitor can be characterized by at least one, two, three, or four of the following: (1) a terminal carbonyl (e.g., carboxylate) so as interact with 5286; (2) a bridging oxygen or similar electron rich atom between a C1 carboxylate and C3 carbonyl of oxaloacetate that provides tight binding through electrostatic and/or hydrogen bonding with R405; (3) a carboxylate or sulfonate at a position corresponding to a C1 carboxylate of oxaloacetate that interacts with R87 and R405; (4) an aromatic and hydrogen bonding interaction at a position corresponding to a C1 carboxylate of phosphoenolpyruvate with Y235 and/or N403.

In one embodiment, the inhibitor can be selected from or include features of 3-[(carboxycarbonyl)oxy]-3-oxopropanoic acid, 3-[(carboxycarbonyl)oxy]propanoic acid, 3-[(carboxymethyl)sulfanyl]-2-oxopropanoic acid, (5,6-dioxo-1,4-dioxan-2-yl)acetic acid, (5,6-dioxo-5,6-dihydro-1,4-dioxin-2-yl)acetic acid, (2-hydroxy-5,6-dioxo-1,4-dioxan-2-yl)acetic acid, salts thereof, acids thereof, or combinations thereof.

In one embodiment, the PEPCK inhibitor is devoid of being characterized by at least one of the following: a methyl or methylene center which, is incapable of interacting with R405; a size incapable of fitting within the binding pocket framed by R87, K244, G237, F333, R405, N403 and/or Y235; a steric conflict with F333; or a positively charged functional group incompatible with a positively charged active site of PEPCK.

In any of the compounds described herein, an aliphatic or backbone carbon can be substituted with O, N, S, or P. Any aliphatic carbon can have a hydrogen replaced with a halogen, Cl, F, $CH_3$, $CH_3CH_2$, or higher or lower substituted or unsubstituted straight chain or branched aliphatic (e.g., C1-C10), an adamantyl (e.g., 2-adamantyl or adamantane derivative), or cycle or heterocycle selected from phenyl, pyridine, pyrimidine, pyrazine, 1,3,5-triazine, 1,2,4-triazine, quinoline, isoquinoline, acridine, phenanthrolines, benzoquinolines, phenathridines, phenazines, quinoxalines, quinazolines, phthalazines, pteridines, cinnolines, pyrroles, imidazoles, 1,2,3-triazoles, 1,2,4, triazoles, tetrazoles, isoxazoles, 1,3-thiazoles, benzimidazoles, indoles, indazoles, benzothiazoles, phenols, naphthols, 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3) oxadiazole, 5-(1,2,3) oxadiazole, 4-(1,2,3) triazole, 5-(1,2,3) triazole, or 2-(1,3,4) thiadiazole.

As used herein, the term "analog", "analogue," or "derivative" is meant to refer to a chemical compound or molecule made from a parent compound or molecule by one or more chemical reactions. As such, an analog can be a compound with a structure similar to that of Compounds 36-41, Formulas A-D, or based on a scaffold thereof.

In one embodiment, each hydrogen on Compounds 36-41, Formulas A-D can be independently replaced with an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like.

As used herein, the term "aliphatic" is meant to refer to a hydrocarbyl moiety, such as an alkyl group, that can be straight or branched, saturated or unsaturated, and/or substituted or unsubstituted, which has twenty or less carbons in the backbone. An aliphatic group may comprise moieties that are linear, branched, cyclic and/or heterocyclic, and contain functional groups such as ethers, ketones, aldehydes, carboxylates, and the like. Exemplary aliphatic groups include but are not limited to substituted and/or unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, alkyl groups of higher number of carbons and the like, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, and the like. The terms aliphatic or alkyl also encompasses alkenyl groups, such as vinyl, allyl, aralkyl and alkynyl groups.

Substitutions within an aliphatic group can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. The aliphatic groups can by way of example also comprise modifications such as azo groups, keto groups, aldehyde groups, carbonyl groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Additionally, the substitutions can be via single, double, or triple bonds, when relevant or possible.

Further, aliphatic groups may also contain hetero substitutions, which are substitutions of carbon atoms, by hetero atoms such as, for example, nitrogen, oxygen, phosphorous, or sulfur. As such, a linker comprised of a substituted aliphatic can have a backbone comprised of carbon, nitrogen, oxygen, sulfur, phosphorous, and/or the like. Heterocyclic substitutions refer to alkyl rings having one or more hetero atoms. Examples of heterocyclic moieties include but are not limited to morpholino, imidazole, and pyrrolidino.

As used herein, the term "aromatic" is meant to refer to molecule is one in which electrons are free to cycle around circular or cyclic arrangements of atoms, which are alternately singly and doubly bonded to one another. More properly, these bonds may be seen as a hybrid of a single bond and a double bond, each bond in the ring being identical to every other. Examples of aromatic compounds that can be present include benzene, benzyl, toluene, xylene, and the like. The aromatic compound can include hetero atoms so as to be a hetero aromatic such as pyridine, furan, tetrahydrofuran, and the like. Also, an aromatic can be a polycyclic aromatic such as naphthalene, anthracene, phenanthrene, polycyclic aromatic hydrocarbons, indole, quinoline, isoquinoline, and the like.

As used herein, the term "amine" is meant to refer to moieties that can be derived directly or indirectly from ammonia by replacing one, two, or three hydrogen atoms by other groups, such as, for example, alkyl groups. Primary amines have the general structures $RNH_2$ and secondary amines have the general structure $R_2NH$. The term amine includes, but is not limited to methylamine, ethylamine, propylamine, isopropylamine, aniline, cyclohexylamine, benzylamine, polycyclic amines, heteroatom substituted aryl and alkylamines, dimethylamine, diethylamine, diisopropylamine, dibutylamine, methylpropylamine, methylhexylamine, methylcyclopropylamine, ethylcylohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

As used herein, the term "halo" means fluoro, chloro, bromo, or iodo, preferably fluoro and chloro.

The present invention is a pharmaceutical agent for the prevention of hyperglycemia in diabetic patients. This will provide a unique agent to alleviate the diabetic complications thus extending life and improving the quality of life of the millions suffering from diabetes. The inhibitor can be selected based on a structure-based design of a central molecular scaffold that is useful for the selective and potent inhibition of the gluconeogenic enzyme PEPCK. The inhibitor scaffold and derivatives thereof can be effective therapeutics against the hyperglycemic condition exhibited by diabetics that leads to all their secondary complications including heart disease and blindness. The structure-based design imparts the inhibitor with selectivity for the target enzyme PEPCK. Thus, the inhibitor will only inhibit PEPCK minimizing side effects due to inhibition of enzymes that utilize similar metabolites. The basic inhibitor scaffold describes a small four carbon molecule whose molecular synthesis is straight forward and economical.

Current therapies for diabetic hyperglycemia are ineffective and wrought with side effects stemming from the fact that the biological target of these agents is not known and thus the agents lack specificity for enzymes involved in the metabolic pathway of glucose synthesis. The inhibitor of the present invention is designed as a potent inhibitor of PEPCK, and since it is a structurally designed inhibitor it is specific to the architecture of the PEPCK active site thus combining potency with specificity which should alleviate side effects due to non-specific inhibition of other biological processes. In one embodiment, the inhibitor does not interact or negatively impact other enzymes outside of the pathway of glucose synthesis.

In one embodiment, the inhibitor can be administered to a diabetic subject in a therapeutically effective amount to treat, inhibit, and/or alleviate the hyperglycemic condition in the diabetic subject. Current treatment of diabetic hyperglycemia involves the use of metformin, sulfonylurease and thiazolidinediones. These therapies exhibit significant side effects include weight gain, gastrointestinal problems, and liver toxicity. Thus, the inhibitor can be administered to a diabetic subject without or lesser effects of weight gain, gastrointestinal problems, and liver toxicity.

Compounds according to the present invention may be used in pharmaceutical compositions having biological/pharmacological activity for the inhibition of PEPCK. These compositions comprise an effective amount of any one or more of the compounds disclosed herein, optionally in combination with a pharmaceutically acceptable additive, carrier, or excipient. Also, the compounds can be combined and/or prepared into pharmaceutically acceptable salts. The compounds may also be co-administered with other therapeutic agents, such as other compounds that inhibit PEPCK. The effective amount can be a therapeutically effective amount of the compound sufficient for use in treating, inhibiting, and/or hyperglycemia in diabetic patients.

As used herein, the terms "an effective amount", "therapeutic effective amount", or "therapeutically effective amount" shall mean an amount or concentration of a compound according to the present invention which is effective within the context of its administration or use. Thus, the term "effective amount" is used throughout the specification to describe concentrations or amounts of compounds according to the present invention which may be used to reduce hyperglycemia in diabetic patients.

As used herein, the term "pharmaceutically acceptable excipient" means an excipient that is useful in preparing a pharmaceutical composition that is generally safe; non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

As used herein, the term "pharmaceutically acceptable acid addition salts" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Any of Compounds 1-41 or derivatives thereof can be prepared as a pharmaceutically acceptable salt.

Groups which form pharmaceutically acceptable acid addition salts include amines, hydrazines, amidines, guanidines, substituted aryl/heteroaryl and substituted alkyl groups that carry at least a nitrogen bearing substituent such as amino, uanidine, amidino, uanidine and the like.

The compounds of the present invention can be formulated into a pharmaceutically acceptable formulation. Such a composition can be useful to prevent, alleviate, eliminate, or delay hyperglycemia in diabetic patients.

In embodiments of the present invention, the pharmaceutical composition comprises an active component and inactive components. The active components are compounds described herein and their derivatives/analogues. The inactive components are selected from the group consisting of excipients, carriers, solvents, diluents, stabilizers, enhancers, additives, adhesives, and combinations thereof.

The amount of the compound in a formulation can vary within the full range employed by those skilled in the art. Typically, the formulation will contain, on a weight percent basis, from about 0.01-99.99 weight percent of the compounds of the present invention based on the total formulation, with the balance being one or more suitable pharmaceutical excipients. Preferably, the compounds are present at a level of about 1-80 weight percent.

Pharmaceutical preparations include sterile aqueous or non-aqueous solutions, suspensions and emulsions. Examples of non-aqueous solvents are propylene glycol, polyethylene glycol, vegetable oil such as olive oil, injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents and inert gases and the like. Those of skill in the art can readily determine the various parameters for preparing these pharmaceutical compositions without resort to undue experimentation.

Pharmacological compositions may be prepared from water-insoluble compounds, or salts thereof, such as aqueous base emulsions. In such embodiments, the pharmacological composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

Additionally, the compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate.

Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multi-dose use. Pharmacological agent compositions for use in practicing the subject methods may be lyophilized using techniques well known in the art.

The compositions may also include components, such as cyclodextrins, to enhance the solubility of one or more other components included in the compositions. Cyclodextrins are widely known in the literature to increase the solubility of poorly water-soluble pharmaceuticals or drugs and/or enhance pharmaceutical/drug stability and/or reduce unwanted side effects of pharmaceuticals/drugs. For example, steroids, which are hydrophobic, often exhibit an increase in water solubility of one order of magnitude or more in the presence of cyclodextrins. Any suitable cyclodextrin component may be employed in accordance with the present invention. The useful cyclodextrin components include, but are not limited to, those materials which are effective in increasing the apparent solubility, preferably water solubility, of poorly soluble active components and/or enhance the stability of the active components and/or reduce unwanted side effects of the active components. Examples of useful cyclodextrin components include, but are not limited to: β-cyclodextrin, derivatives of β-cyclodextrin, carboxymethyl-β-cyclodextrin, carboxymethyl-ethyl-β-cyclodextrin, diethyl β-cyclodextrin, dimethyl-β-cyclodextrin, methyl-β-cyclodextrin, random methyl-β-cyclodextrin, glucosyl β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof.

The specific cyclodextrin component selected should have properties acceptable for the desired application. The cyclodextrin component should have or exhibit reduced toxicity, particularly if the composition is to be exposed to sensitive body tissue, for example, eye tissue, etc. Very useful β-cyclodextrin components include β-cyclodextrin, derivatives of β-cyclodextrin and mixtures thereof. Particularly useful cyclodextrin components include sulfobutylether β-cyclodextrin, hydroxypropyl cyclodextrin and mixtures thereof. Sulfobutylether β-cyclodextrin is especially useful, for example, because of its substantially reduced toxicity.

The pharmaceutically acceptable excipients, such as vehicles, adjuvants, carriers or diluents, are readily available to the public. Examples of suitable excipients can include, but are not limited to, the following: acidulents, such as lactic acid, hydrochloric acid, and tartaric acid; solubilizing components, such as non-ionic, cationic, and anionic surfactants; absorbents, such as bentonite, cellulose, and kaolin; alkalizing components, such as diethanolamine, potassium citrate, and sodium bicarbonate; anticaking components, such as calcium phosphate tribasic, magnesium trisilicate, and talc; antimicrobial components, such as benzoic acid, sorbic acid, benzyl alcohol, benzethonium chloride, bronopol, alkyl parabens, cetrimide, phenol, phenylmercuric acetate, thimerosol, and phenoxyethanol; antioxidants, such as ascorbic acid, alpha tocopherol, propyl gallate, and sodium metabisulfite; binders, such as acacia, alginic acid, carboxymethyl cellulose, hydroxyethyl cellulose; dextrin, gelatin, guar gum, magnesium aluminum silicate, maltodextrin, povidone, starch, vegetable oil, and zein; buffering components, such as sodium phosphate, malic acid, and potassium citrate; chelating components, such as EDTA, malic acid, and maltol; coating components, such as adjunct sugar, cetyl alcohol, polyvinyl alcohol, carnauba wax, lactose maltitol, titanium dioxide; controlled release vehicles, such as microcrystalline wax, white wax, and yellow wax; desiccants, such as calcium sulfate; detergents, such as sodium lauryl sulfate; diluents, such as calcium phosphate, sorbitol, starch, talc, lactitol, polymethacrylates, sodium chloride, and glyceryl palmitostearate; disintegrants, such as colloidal silicon dioxide, croscarmellose sodium, magnesium aluminum silicate, potassium polacrilin, and sodium starch glycolate; dispersing components, such as poloxamer 386, and polyoxyethylene fatty esters (polysorbates); emollients, such as cetearyl alcohol, lanolin, mineral oil, petrolatum, cholesterol, isopropyl myristate, and lecithin; emulsifying components, such as anionic emulsifying wax, monoethanolamine, and medium chain triglycerides; flavoring components, such as ethyl maltol, ethyl vanillin, fumaric acid, malic acid, maltol, and menthol; humectants, such as glycerin, propylene glycol, sorbitol, and triacetin; lubricants, such as calcium stearate, canola oil, glyceryl palmitostearate, magnesium oxide, poloxymer, sodium benzoate, stearic acid, and zinc stearate; solvents, such as alcohols, benzyl phenylformate, vegetable oils, diethyl phthalate, ethyl oleate, glycerol, glycofurol, for indigo carmine, polyethylene glycol, for sunset yellow, for tartazine, triacetin; stabilizing components, such as cyclodextrins, albumin, xanthan gum; and tonicity components, such as glycerol, dextrose, potassium chloride, and sodium chloride; and mixture thereof. Excipients include those that alter the rate of absorption, bioavailability, or other pharmacokinetic properties of pharmaceuticals, dietary supplements, alternative medicines, or nutraceuticals.

Other examples of suitable excipients, binders and fillers are listed in Remington's Pharmaceutical Sciences, 18th Edition, ed. Alfonso Gennaro, Mack Publishing Co. Easton, Pa., 1995 and Handbook of Pharmaceutical Excipients, 3rd Edition, ed. Arthur H. Kibbe, American Pharmaceutical Association, Washington D.C. 2000, both of which are incorporated herein by reference.

In some embodiments, the compounds in the compositions may be present as a pharmaceutically acceptable salt. The term "pharmaceutically acceptable salts" includes salts of the composition, prepared, for example, with acids or bases, depending on the particular substituents found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galactunoric, salicylic, formic, naphthalene-2-sulfonic, and the like. Still other suitable acids include amino acids such as arginate, aspartate, glutamate, and the like.

In general, pharmaceutically acceptable carriers for are well-known to those of ordinary skill in the art. This carrier can be a solid or liquid and the type is generally chosen based on the type of administration being used. Suitable pharmaceutical carriers are, in particular, fillers, such as sugars, for example lactose, sucrose, mannitol or sorbitol, cellulose preparations and/or calcium phosphates, for example tricalcium phosphate or calcium hydrogen phosphate, furthermore, binders such as starch paste, using, for example, corn, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example, to identify or to indicate different doses of active ingredient, may be added to the tablets or sugar-coated tablet coatings.

Additional pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Additional formulations for use in the present invention can be found in Remington's Pharmaceutical Sciences (Mack Publishing Company, Philadelphia, Pa., 17th ed. (1985)), which is incorporated herein by reference. Moreover, for a brief review of methods for drug delivery, see, Langer, Science 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. Other examples of suitable pharmaceuticals are listed in 2000 Med Ad News 19:56-60 and The Physicians Desk Reference, 53rd edition, 792-796, Medical Economics Company (1999), both of which are incorporated herein by reference.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. One manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of this invention is inhalation.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilizers.

Suitable rectally utilizable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 (herein incorporated by reference) describes a pharmaceutical formulation having particles in the size range from 10 to 1,000 nm in which the active material is supported on a crosslinked matrix of macromolecules. U.S. Pat. No. 5,145,684 (herein incorporated by reference) describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

According to the methods of the present invention, the compositions of the invention can be administered by injection by gradual infusion over time or by any other medically acceptable mode. Any medically acceptable method may be used to administer the composition to the patient. The particular mode selected will depend of course, upon factors such as the particular drug selected, the severity of the state of the subject being treated, or the dosage required for therapeutic efficacy. The methods of this invention, generally speaking, may be practiced using any mode of administration that is medically acceptable, meaning any mode that produces effective levels of the active composition without causing clinically unacceptable adverse effects.

The administration may be localized (i.e., to a particular region, physiological system, tissue, organ, or cell type) or systemic. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be used for some treatments because of the convenience to the patient as well as the dosing schedule. Compositions suitable for oral administration may be presented as discrete units such as capsules, pills, cachettes, tables, or lozenges, each containing a predetermined amount of the active compound. Other oral compositions include suspensions in aqueous or non-aqueous liquids such as syrup, an elixir, or an emulsion.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules; emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds can be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulator agents such as suspending, stabilizing and/or dispersing agents.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds can be encapsulated in a vehicle such as liposomes that facilitates transfer of the bioactive molecules into the targeted tissue, as described, for example, in U.S. Pat. No. 5,879,713 to Roth et al. and Woodle, et al., U.S. Pat. No. 5,013,556, the contents of which are hereby incorporated by reference. The compounds can be targeted by selecting an encapsulating medium of an appropriate size such that the medium delivers the molecules to a particular target. For example, encapsulating the compounds within microparticles, preferably biocompatible and/or biodegradable microparticles, which are appropriate sized to infiltrate, but remain trapped within, the capillary beds and alveoli of the lungs can be used for targeted delivery to these regions of the body following administration to a patient by infusion or injection.

Microparticles can be fabricated from different polymers using a variety of different methods known to those skilled in the art. The solvent evaporation technique is described, for example, in E. Mathiowitz, et al., J. Scanning Microscopy, 4, 329 (1990); L. R. Beck, et al., Fertil. Steril., 31, 545 (1979); and S. Benita, et al., J. Pharm. Sci., 73, 1721 (1984). The hot-melt microencapsulation technique is described by E. Mathiowitz, et al., Reactive Polymers, 6, 275 (1987). The spray drying technique is also well known to those of skill in the art. Spray drying involves dissolving a suitable polymer in an appropriate solvent. A known amount of the compound is suspended (insoluble drugs) or co-dissolved (soluble drugs) in the polymer solution. The solution or the dispersion is then spray-dried. Microparticles ranging between 1-10 microns are obtained with a morphology which depends on the type of polymer used.

Microparticles made of gel-type polymers, such as alginate, can be produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath to allow sufficient time for gelation to occur. Microparticle particle size is controlled by using various size extruders or varying either the nitrogen gas or polymer solution flow rates.

Particle size can be selected according to the method of delivery which is to be used, typically size IV injection, and where appropriate, entrapment at the site where release is desired.

In one embodiment, the liposome or microparticle has a diameter which is selected to lodge in particular regions of the body. For example, a microparticle selected to lodge in a capillary will typically have a diameter of between 10 and 100, more preferably between 10 and 25, and most preferably, between 15 and 20 microns. Numerous methods are known for preparing liposomes and microparticles of any particular size range. Synthetic methods for forming gel microparticles, or for forming microparticles from molten materials, are known, and include polymerization in emulsion, in sprayed drops, and in separated phases. For solid materials or preformed gels, known methods include wet or dry milling or grinding, pulverization, classification by air jet or sieve, and the like.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, injection etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert at least one pharmacological agent into the delivery device for administration of the pharmacological agent to a subject and include, but are not limited to, vials, ampules, tubes, capsules, bottles, syringes and bags.

Sterile injectable forms of the compositions of this invention may be aqueous or a substantially aliphatic suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. Pharmacological agent formulations suitable for transdermal administration may also be delivered by iontophoresis and may take the form of an optionally buffered aqueous solution of the pharmacological agent compound. Suitable formulations may include citrate or bis/tris buffer (pH 6) or ethanol/water and contain a suitable amount of active ingredient. Topical application for the lower intestinal tract can be effected in a rectal suppository formulation (see above) or in a suitable enema formulation. Topically-transdermal patches may also be used.

For other topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or, more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl αalcohol or other suitable preservatives, absorption promoters to enhance bioavailability, fluorocarbons, and/or other conventional solubilizing or dispersing agents.

Depending on the mode of administration, the pharmaceutical composition will preferably comprise from 0.05 to 99% by weight, more preferably from 0.1 to 70% by weight of the active ingredient, and, from 1 to 99.95% by weight, more preferably from 30 to 99.9% by weight of a pharmaceutically acceptable carrier, all percentages being based on the total composition.

The compositions of the present invention may be given in dosages, generally at the maximum amount while avoiding or minimizing any potentially detrimental side effects. The compositions can be administered in effective amounts, alone or in a cocktail with other compounds, for example, other compounds that can be used to treat and/or prevent hyperglycemia in diabetic patients. An effective amount is generally an amount sufficient to inhibit hyperglycemia in diabetic patients.

In one embodiment of the present invention, therapeutically effective amounts of compounds of the present invention may range from approximately 0.05 to 50 mg per kilogram body weight of the recipient per day; preferably about 0.01-25 mg/kg/day, more preferably from about 0.5 to 10 mg/kg/day. Thus, for administration to a 70 kg person, the dosage range would most preferably be about 35-70 mg per day.

In another embodiment of the present invention, dosages may be estimated based on the results of experimental models, optionally in combination with the results of assays of the present invention. Generally, daily oral doses of active compounds will be from about 0.01 mg/kg per day to 2000 mg/kg per day. Oral doses in the range of 10 to 500 mg/kg, in one or several administrations per day, may yield suitable results. In the event that the response of a particular subject is insufficient at such doses, even higher doses (or effective higher doses by a different, more localized delivery route) may be employed to the extent that patient tolerance permits. Multiple doses per day are also contemplated in some cases to achieve appropriate systemic levels of the composition. Dosage amount and interval may be adjusted individually to provide plasma levels of the active compound which are sufficient to maintain therapeutic effect. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

Although the exact dosage will be vary dependent upon the percent composition of the dosage of compounds of the present invention, in most cases some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro and in vivo data. Dosages necessary to achieve the MEC will depend on individual characteristics and route of administration. However, HPLC assays or bioassays can be used to determine plasma concentrations.

Use of a long-term release implant may be particularly suitable in some cases. "Long-term release," as used herein, means that the implant is constructed and arranged to deliver therapeutic levels of the composition for at least 30 or 45 days, and preferably at least 60 or 90 days, or even longer in some cases. Long-term release implants are well known to those of ordinary skill in the art, and include some of the release systems described above.

Any suitable dosage may be administered. The compound, the carrier, and the amount will vary widely depending on body weight, the severity of the condition being treated and other factors that can be readily evaluated by those of skill in the art. Generally a dosage of between about 1 mg per kg of body weight and about 100 mg per kg of body weight is suitable.

In pharmaceutical dosage forms, agents may be administered alone or with an appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time. The pharmacological agent and at least one other adjuvant may be administered simultaneously (i.e., concurrently) or sequentially. Simultaneous administration may be carried out by mixing at least one pharmacological agent and at least one other adjuvant prior to administration, or by administering the pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population), the $ED_{50}$ (the dose therapeutically effective in 50% of the population), and $EC_{50}$ (the excitatory concentration effective in 50% of the population). The dose ratio between toxic and therapeutic effect is the therapeutic index and can be expressed as the ratio between $LD_{50}$ and $ED_{50}$. Compounds which exhibit high therapeutic indices are candidates for further development. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: "The Pharmacological Basis of Therapeutics", Ch. 1, p. 1). Additionally, the $EC_{50}$ can be important to measure.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

The exact formulation, route of administration and dosage for the pharmaceutical compositions of the present invention can be chosen by the individual physician in view of the patient's condition. (See e.g., et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $EC_{50}$, $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to hyperglycemia in diabetic patients, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

Experiments

Various materials were used in the experiments to study the structure-function of molecules to inhibit PEPCK. The compounds used in this study are shown in Table 1, which includes their name and chemical formulae. Compounds I-6, 8,9,12, 17-27, and 29 were from Aldrich Chemicals; Compounds 14, 15, and 32 were from Fluka; Compounds 10, 11, 13, 16, and 33-35 were from Sigma; Compounds 7 and 23 were from Kodak; Compound 28 was from Mallinckrodt; Compound 30 was from Alfa; and Compound 31 was from Pfaltz and Bauer. All compounds were of the highest commercially available purity. The buffers TES and HEPES were from Research Organics. DTT, PEP, IDP, and TRIS were from Sigma. OAA and NADH were from Boehringer Mannheim.

Various enzymes were used in the experiments to study the structure-function of molecules to inhibit PEPCK. Malate dehydrogenase (1200 units/mg; 50% glycerol solution, v:v) was from Boerhinger Mannheim. PEPCK utilized for the kinetic studies was purified to homogeneity from rat liver cytosol following published procedures (Colombo, G., Carlson, G. M., and Lardy, H. A. (1978) Phosphoenolpyruvate carboxykinase (guanosine triphosphate) from rat liver cytosol. Separation of homogeneous forms of the enzyme with high and low activity by chromatography on agarose-hexane-guanosine triphosphate. *Biochemistry* 17, 5321-5329; Lewis, C. T., Seyer, J. M., and Carlson, G. M. (1989) Cysteine 288: an essential hyperreactive thiol of cytosolic phosphoenolpyruvate carboxykinase (GTP). *J Biol Chem* 264, 27-33), with the following modifications. Frozen livers from 24-h fasted male Wystar rats were purchased from Pel-Freeze. The final purification of the enzyme by affinity chromatography on agarose-adipic acid-GTP (Sigma) was performed by eluting with a NaCl step gradient (100 mM to 500 mM, in 100 mM increments) in 10 mM. TES (pH 7.2), 7.5% glycerol (v:v), 0.2 mM EDTA. This procedure afforded enzyme of >95% purity, based on SDS-PAGE analysis. The enzyme preparation routinely had a specific activity of 16-24 µM of OAA formed/min/mg protein at 25° C. Solutions of enzyme were saturated with nitrogen and stored at 5° C. Under these conditions, the enzyme was stable for 2-3 weeks. The concentration of PEPCK was determined spectrophotometrically, using a molar extinction coefficient of $1.15 \times 10^5$. The enzyme utilized for the crystallographic studies was recombinantly expressed in and purified from *E. coli* cells as previously described (Sullivan, S. M., and Holyoak, T. (2007) Structures of rat cytosolic PEPCK: Insight into the mechanism of phosphorylation and decarboxylation of oxaloacetic acid. Biochemistry 46, 10078-10088).

Molecules were studied in order to identify molecular features for interacting with an inhibiting PEPCK. The inhibition of PEPCK by various compounds was evaluated using a continuous spectrophotometric assay in which the coupling enzyme, malate dehydrogenase, reduced OAA to malate concomitant with the oxidation of NADH to $NAD^+$. The decrease in absorbance at 340 nm was monitored using a Beckman DU-70 Spectrophotometer equipped with a temperature controller. The standard 1-mL reaction mixture for the production of OAA contained 56 mM HEPES-KOH buffer (pH 7.0), 1 mM IDP (or alternatively, 0.1 mM GDP), 23 U malate dehydrogenase (1 unit of malate dehydrogenase is defined as 1 mole malate produced/min/mg protein), 0.25 mM NADH, 2.3 mM $MnCl_2$, and 48 mM $NaHCO_3$. Under these conditions, PEP was the varied substrate. When IDP was the varied substrate for the determination of the pattern of inhibition for pyrophosphate, the fixed PEP concentration was 2 mM. Each molecule tested for interaction with and/or inhibition of PEPCK was included in a solution freshly prepared in 50 mM HEPES-KOH (pH 7.0), and these stock solutions were diluted in the same buffer, with the pH being maintained. All assay components except PEPCK were preincubated in the cuvette for 3 min at 35° C., the standard assay temperature. This temperature was used because, during pilot experiments with the inhibitor phosphonoformate, greater inhibition was observed at 35° C. than at 20° C. Similarly, Nowak and Mildvan (Nowak, T., and Mildvan, A. S. (1970) Stereoselective interactions of phosphoenolpyruvate analogues with phosphoenolpyruvate-utilizing enzymes. J Biol Chem 245, 6057-6064) demonstrated that inhibition of yeast enolase by the PEP analogue phosphoglycolate was also temperature-dependent. In our study, the reaction was initiated by addition of enzyme (10 µL of a 0.3 µM or 1.5 µM solution diluted with 10 mM TES (pH 7.2), 0.2 mM DTT, 0.2 mM EDTA, and 7.5% glycerol (v:v). The specific activity of enzyme in the inhibition studies is expressed as µmoles OAA formed/min/mg protein. Assays to determine patterns of inhibition were performed in triplicate. Unless otherwise stated, titration experiments to estimate the concentration of inhibitor that caused 50% inhibition of PEPCK activity were performed in duplicate. At the highest concentrations used with PEPCK, none of the compounds evaluated in this study affected the activity of the coupling enzyme, malate dehydrogenase.

The kinetic parameters for the inhibition studies were best fit to the equations for competitive inhibition (Eq. 1) and noncompetitive inhibition (Eq. 2), using the computer program and nomenclature of Cleland (Cleland, W. W. (1979) Statistical analysis of enzyme kinetic data. *Methods Enzymol* 63, 103-138).

$$v = VA/[K(1+1/K_{is})+A] \tag{Eq. 1}$$

$$v = VA/[K(1/K_{is})+A(1+1/K_{ii})] \tag{Eq. 2}$$

The parameters are defined as follows: v is the initial velocity, V is the maximal rate of product formation in the absence of inhibitor, A is the concentration of the variable substrate, K is the apparent Michaelis constant for the varied substrate, and $K_{is}$ and $K_{ii}$ are the inhibition constants.

For weakly inhibitory analogues for which a complete inhibition pattern was not determined, Dixon plots were used to determine $K_i$ values Segal, I. H. (1976) in Biochemical Calculations pp 246-273, John Wiley & Sons, New York.

Crystals of PEPCK used for data collection were grown by the hanging-drop method at 25° C. by mixing 4 µL of protein [containing 10 mg/mL PEPCK, 25 mM HEPES (pH 7.5) and 1 mM DTT] with 2 µL mother liquor [0.1 M HEPES (pH 7.4) and 16-24% PEG 3350 and 0.5 µL of 0.1 M $MnCl_2$]. The crystals of the various inhibitor complexes were obtained and cryoprotected simultaneously by transferring the crystals to 20 µL drops containing 25% PEG 3350, 10% PEG 400, 0.1 M Hepes pH 7.5, 2 mM $MnCl_2$, and 10 mM of oxalate, PGA, phosphonoformate, phosphonopropionate, or sulfoacetate for 1 hour prior to cryocooling in liquid nitrogen.

Data on the cryocooled crystals at −180° C. were collected using a RU-H3R rotating Cu anode X-ray generator with Blue Confocal Osmic Mirrors and a Rigaku Raxis IV++ detector. All data was integrated and scaled with HKL-2000(21). Data statistics are presented in Table 2.

The new structures of the rat cPEPCK were determined by molecular replacement using MOLREP (Vagin, A., and Teplyakov, A. (1997) MOLREP: an automated program for molecular replacement. *J Appl Cryst* 30, 1022-1025) in the CCP4 (Bailey, S. (1994) The Ccp4 Suite—Programs for Protein Crystallography. *Acta Cryst* D50, 760-763) package and the previously determined structure of rat cPEPCK (PDB 2QEW). This molecular replacement solution was refined using Refmac5 followed by manual model adjustment and rebuilding using COOT (Emsley, P., and Cowtan, K. (2004) Coot: model-building tools for molecular graphics. *Acta Cryst* D60, 2126-2132). Ligand, metal, and water addition and validation were also performed in COOT. Inspection of the $F_o-F_c$ maps indicated that in the PEPCK-$Mn^{2+}$-PGA structure, two conformations of bound PGA were present in each of the two molecules in the ASU. The occupancy of the two conformations was manually adjusted (0.5) to minimize positive and negative difference density peaks in the maps. The occupancy and B-factors for the ligands are given in Table 2.

A final round of TLS refinement was performed for all models in Refmac5. A total of 15 groups were utilized per chain in the PEPCK-$Mn^{2+}$-oxalate, PEPCK-$Mn^{2+}$-phosphonoformate, PEPCK-$Mn^{2+}$-phosphonopropionate, and PEPCK-$Mn^{2+}$-sulfoacetatate structures while 10 groups per chain were utilized in the refinement of the PEPCK-$Mn^{2+}$-PGA structure. The optimum TLS groups were determined by submission of the pdb files to the TLSMD server (skuld.bmsc.washington.edu/~tlsmd/index.html; Painter, J., and Merritt, E. A. (2005) A molecular viewer for the analysis of TLS rigid-body motion in macromolecules. Acta Cryst D61, 465-471). In structures containing two molecules in the ASU, tight NCS restraints were utilized during the initial rounds of refinement and were removed during the final stages of refinement. All the models have excellent stereochemistry as determined by PROCHECK (Laskowski, R. A., Macarthur, M. W., Moss, D. S., and Thornton, J. M. (1993) Procheck—a Program to Check the Stereochemical Quality of Protein Structures. *J Appl Cryst* 26, 283-291). Final model statistics are presented in Table 2.

The initial preliminary screening of the compounds listed in Table 1 involved comparison of their structural similarities to OAA and PEP. One of the criteria in choosing inhibitor compounds was that the inhibitors of PEPCK possess functional groups similar to those of the OAA and PEP substrates. Thus, with the exception of three compounds (Compounds 33-35), the molecules screened were bifunctional (e.g., bicarboxylates, biphosphonates, or bisulfonates) or else monocarboxylates with phosphonyl or sulfonyl groups as additional anionic moieties. A second criterion was size (e.g., molecular volume and length). Bifunctional compounds with conjugated ring systems or with more than six backbone carbons were excluded. Many of the compounds evaluated have not been utilized previously, and thus represent new reversible inhibitors of rat liver cPEPCK.

Inhibition was initially screened using a Dixon plot at a fixed PEP concentration of 40 µM (½ $K_m$) and inhibitors from 1.5 to 6.0 mM. Unless otherwise stated, those molecules that caused less than 30-40% inhibition were not further studied (Table 1), although their inability to inhibit will be discussed. For the molecules that caused greater inhibition, the pattern of inhibition was determined using PEP or IDP as the varied substrate (Table 3).

Some of the molecules that inhibit PEPCK include oxaloacetate analogues. Oxalate (Table 1, Compound I) is a competitive inhibitor of PEPCK with a $K_i$ of 89 µM (Table 3). This value is similar to that of the $K_m$ for PEP (82 µM) determined under the same conditions (data not shown). In a previous study, oxalate was also found to be a competitive inhibitor with respect to OAA of the rat liver cPEPCK, with a K, equivalent to the $K_m$ for OAA (Ash, D. E., Emig, F. A., Chowdhury, S. A., Satoh, Y., and Schramm, V. L. (1990) Mammalian and Avian Liver Phosphoenolpyruvate Carboxykinase—Alternate Substrates and Inhibition by Analogs of Oxaloacetate. *J Biol Chem* 265, 7377-7384). Because of oxalate's resemblance to the enolate of pyruvate, a postulated reaction intermediate generated during the conversion of PEP to pyruvate (Reed, G. H., and Morgan, S. D. (1974) Kinetic and magnetic resonance studies of the interaction of oxalate with pyruvate kinase. *Biochemistry* 13, 3537-3541), this analogue has been previously studied and found to be a reversible inhibitor of PEP-dependent enzymes. Crystallographic studies of Anaerobiospirillum succiniciproducens (Cotelesage, J. J. H., Prasad, L., Zeikus, J. G., Laivenieks, M., and Delbaere, L. T. J. (2005) Crystal structure of Anaerobiospirillum succiniciproducens PEP carboxykinase reveals an important active site loop. *Int J Biochem Cell Biol* 37, 1829), in addition to the structure of rat PEPCK in complex with oxalate presented here, demonstrate that oxalate binds to the active site manganese in a bidentate fashion directly coordinating to the metal through the C1 and C2 carbonyl oxygens in an identical orientation to that of the central skeleton of the substrate OAA (FIGS. 1A-1F). This conformation leaves one water molecule coordinated to the active site metal, which is subsequently displaced by the γ-phosphoryl oxygen of GTP. Itaconate, the vinyl analogue of OAA, did not inhibit (Table 1, Compound 7), suggesting that the C3 keto oxygen present in the substrate (replaced by a methylene group in itaconic acid) is essential for the interaction of the ligand with PEPCK through direct coordination with the active site $Mn^{2+}$ ion. Although the complete patterns of inhibition were not determined for the poor inhibitors succinate and maleate (Table 1, Compounds 3 and 5), $K_i$ values were obtained from Dixon plots, using two concentrations of PEP (Table 3). Succinate had a $K_i$ value greater than 8 mM, whereas that for maleate was approximately 2 mM. Fumarate, the trans-isomer of maleate, did not inhibit PEPCK (Table 1, Compound 6). The lack of inhibition by 1,2-cyclopentanedicarboxylate (Compound 8) was likely due to the bulkiness of its cyclic moiety. These results are in agreement with previous findings in which putative OAA analogues were usually poor inhibitors, with $K_i$ values above 6 mM (Hebda, C. A., and Nowak, T. (1982) The purification, characterization, and activation of phosphoenolpyruvate carboxykinase from chicken liver mitochondria. J Biol Chem 257, 5503-5514; Hebda, C. A., and Nowak, T. (1982) Phosphoenolpyruvate carboxykinase. Mn2+ and Mn2+ substrate complexes. J Biol Chem 257, 5515-5522).

Taken together with the structural data, the relatively poor inhibition by the putative OAA analogues used in this and other studies demonstrates that the enzyme is relatively intolerant of changes in the bicarboxylate structure. The structure of oxalate, in combination with the lack of inhibition by itaconate and the other OAA analogues demonstrates clearly the importance of the two planar cis-carbonyl groups. The structural data demonstrate that these $sp^2$-hybridized centers are necessary for the cis-planar geometry (O—C—C—O torsion=–9.6° that is required to displace the previously bound water molecules in a perfect example of entropy-entropy compensation. Further, this planar geometry is the only geometry that allows for the conjugation of the carbonyl groups and the ability to delocalize electrons through the metal center.

With the exception of oxalate, all of the OAA analogues tested, while retaining a bicarboxylate electronic structure, lack this central feature and therefore would be deficient in forming the OAA-like conformation that appears to be a central motif for tight binding of ligands directly to the active site manganese ion. Note the poor/lack of inhibition by malonate, maleate and succinate (Tables 1 and 3). This conclusion is further supported by previous work in which lactate, malate, nitrolactate, glycerate, thioglycolate, µ-chlorolactate, and glycolate, all of which contain an $sp^3$ hybridized center alpha to the terminal carboxylate, are either poor substrates or poor inhibitors of mPEPCK. Additional support for this conclusion comes from the observation that only one carboxylate interacts with the active site manganese ion in the mPEPCK-$Mn^{2+}$-malonate-$Mn^{2+}$GDP structure in a geometry vastly different than that of OAA/oxalate.

While the cis-$sp^2$ carbonyls are necessary for micromolar inhibition, they are not the only requirement. As has been demonstrated previously, pyruvate (and its 8-mercapto-, fluoro-, nitro-, and hydroxy-derivatives), glyoxylate, α-ketobutyrate, α-ketoglutarate and acetopyruvate are poor or noninhibitory compounds, despite containing the cis $sp^2$ hybridized carbonyl centers. While acetopyruvate and α-ketoglutarate are likely excluded from the active site due to their large size, the other compounds are isoelectronic with OAA and would be predicted to bind more tightly than is observed based upon the above conclusion. The structural data again provide an explanation for this dramatic reduction of 100-1000 fold in binding affinity ($K_i$ oxalate=5-89 μM ($K_i$ pyruvate=9 mM).

Comparing the tight binding analogues oxalate and phosphonoformate, it is observed that they both posses an oxygen anion that forms two short hydrogen bonds in addition to an electrostatic interaction with R405 (FIGS. 1A-1F). In contrast, all of the poor inhibitors mentioned above that contain the correct cis $sp^2$ carbonyl structure either lack this oxygen (i.e. glyoxylate) or have a methyl or methylene center, which is incapable of taking advantage of the R405 interactions that appear to be worth between 3-4 kcal mol$^{-1}$ of binding energy. As OAA contains a methylene center alpha to the $sp^2$ carbonyl, it raises the question of how OAA achieves the reasonable $K_m$ of ~2-5 μM if the aforementioned interaction is necessary for tight binding. The structure with OAA demonstrates that compensation for the lack of interaction between R405 and the C2 methylene group arises from interactions between R405 and/or R87 with the C1 carboxylate of OAA. The other inhibitors either do not posses a C1 carboxylate (e.g., pyruvate and its derivatives and α-ketobutyrate) or the group is not spatially located to correctly interact in a similar fashion (e.g., α-ketoglutarate). This results in the observed poor inhibition by these molecules even in the presence of the cis carbonyl structure. This conclusion is further supported by the observation that β-sulfopyruvate is a tight binding inhibitor of mPEPCK, suggesting that the S-sulfo group effectively mimics the C1 carboxylate of OAA and therefore binds to the enzyme with a $K_i$ similar to the $K_m$ of OAA ($K_i$=19-138 μM).

Phosphonoformate (Table 1, Compound 10) is a competitive inhibitor of PEPCK with a $K_i$ of 231 μM (Table 3). While initially chosen as a mimic of PEP, the structural data clearly show the interaction of phosphonoformate in a mode similar to that observed for OAA and oxalate (FIG. 1B). This appears to be a result of the O3 of the phosphono group and the C1 carbonyl forming the same central cis-planar oxygen geometry (O—C—P—O torsion=−14.6°) as in oxalate and OAA. In addition, consistent with the mechanism of recognition discussed above, the other carboxylate and phosphonate oxygens of phosphonoformate form similar electrostatic and hydrogen bonding interactions with R87 and R405 to those of oxalate, resulting in similar micromolar inhibition (Table 3). The slightly greater distortion from planar found in the cis carbonyl centers of phosphonoformate as compared to oxalate may explain the approximately 2-fold greater $K_i$ observed with phosphonoformate.

It has been found that phosphoenolpyruvate analogues can be PEPCK inhibitors. Phosphoglycolate (PGA, Table 1, Compound 13) is a competitive inhibitor of PEPCK, with a $K_i$ value of 1.04 mM (Table 3). Because of its marked resemblance to PEP in terms of molecular geometry, volume, and identical functional groups, PGA has been used previously as an alternative substrate or reversible inhibitor of PEP-dependent enzymes. Not surprisingly, the structural data show a binding mode of PGA that is similar in the general orientation of the ligand to that of PEP, with the phosphate coordinating to the active site manganese ion and the ligand extending away from the ion toward Y235 (FIGS. 1C-1D). Unlike the other inhibitor complexes, the PGA bound to PEPCK is statically disordered and found in two different conformations in each molecule in the ASU. While one conformation is virtually identical to the bound conformation of 3-phosphonopropionate (Compound 12), the other conformation is unique to PGA and has the phosphate group situated in a position similar to its location in the PEPCK-$Mn^{2+}$-PEP complex (data not shown). As 3-phosphonopropionate is the phosphonate analogue of PGA and the two compounds are structurally similar, this additional conformation and static disorder in PGA must be due to the presence of the bridging phosphate oxygen that is absent in 3-phosphonopropionate. This conclusion is confirmed by the structural data demonstrating that the presence of the bridging phosphate oxygen atom in PGA results in the formation of a hydrogen bond with either the NH1 or NH2 group of R405 in the two bound conformations respectively. The conformation of bound inhibitor that is shared by PGA and 3-phosphonopropionate appears to be the result of the loss of the unsaturated C3 methylene group that is present in PEP. This removes an apparent aromatic interaction between the methylene group and F333 and allows the PGA and 3-phosphonopropionate inhibitors to shift in the binding pocket in a direction toward F333. This displacement in the conformation of bound PGA and 3-phosphonopropionate shown in FIGS. 1C-1D results in an additional difference between the bound conformation of the inhibitors and that of PEP. While PEP is found to interact indirectly with the active site metal ion through two coordinating water molecules, one phosphate/phosphono oxygen of PGA and 3-phosphonopropionate displaces one of the metal coordinated water molecules, resulting in the phosphate/phosphono group coordinating directly to the manganese center. This change in metal coordination of the bound PGA and 3-phosphonopropionate inhibitors results in the loss of the Y235-carboxylate aromatic interaction and the hydrogen bond between the carboxylate and the side chain amide of N403 that, based upon the difference in the $K_m$ for PEP (82 μM) and the $K_i$ for the PGA and 3-phosphonopropionate (1-2 mM), appear to be responsible for at least 1.4 kcal mol$^{-1}$ of binding energy.

Phosphonoacetate (Compound 11), a methylene homologue of phosphonoformate is noninhibitory; however as mentioned above, the next larger methylene homologue of phosphonoacetate, 3-phosphonopropionate (Compound 12), is inhibitory, with a $K_i$ value of 1.9 mM (Table 3). The similar inhibitory capability of 3-phosphonopropionate and PGA (Table 3) is consistent with the similar size and hybridization state of the bridging methylene group and oxygen atom of the two compounds. Also, as discussed above, the structure of PEPCK in complex with 3-phosphonopropionate shows a virtually identical bound conformation to that of PGA, again consistent with their similar millimolar inhibition constants (FIG. 1E). Unlike what is observed with PGA versus 3-phosphonopropionate, the methylene analogue of PEP, 2-(phosphonomethyl)acrylate, is noninhibitory (Table 1, Compound 15). This lack of inhibition is most likely the result of the inability of this longer inhibitor to fit within the PEP binding pocket.

2-D-Phosphoglycerate is also noninhibitory (Table 1, Compound 14). This analogue is similar to phosphoglycolate, except for the replacement of a C2 hydrogen with the larger —$CH_2OH$ group, whose introduction would interfere with binding at the PEP site through a steric effect. Another analogue with a bulky group at the C2 position, 2-amino-3-phosphonopropionate (Compound 18), likewise fails to inhibit, even though 3-phosphonopropionate is moderately inhibitory. Both 2-amino-3-phosphonopropionate and 3-phosphonopropionate also have the added negative factor of a methylene bridge between C2 and the phosphoryl group. The bridging methylene group in itself hinders binding (compare Compound 15 with PEP); nevertheless, a negative effect of amino substitution at C2 can also be observed by comparing Compounds 25 and 26. Because the C2 carbons in 2-D-phosphoglycerate and 2-amino-3-phosphonopropionate are chiral, one might infer that the lack of inhibition could be reversed by using the L-isomer, at least in the case of phosphoglycerate. Studies have shown that the D- and L-isomers of PEP analogues inhibit some PEP-dependent enzymes differently; however, in the experiment using the noninhibitory 2-amino-3-phosphonopropionate, a racemic mixture was used. No inhibition is observed with any dicarboxylates or phosphonyl monocarboxylates that contain an amino group (Table 1, Compounds 9, and 18-22), although all of these compounds are rather bulky (relatively large volumes and lengths). The analogue 6-phosphonogluconate (Compound 16) also does not inhibit, presumably due to its increased molecular volume and length. The lack of inhibition by these compounds illustrates the tight geometric constraints placed upon the substitution at the C2 carbon of PEP. The active site pocket for PEP is framed by R87, K244, G237, F333, R405, N403 and Y235. The structural data suggest that substitutions at C2 are limited, as these substitutions in the location of the C2 proton of PEP would sterically conflict with R87. Similarly, substitutions at the site corresponding to the C3 methylene group of PEP would seem to be limited to the native methylene group because of steric conflict with F333.

It has been found that sulfonyl monocarboxylates can be PEPCK inhibitors. A priori, these compounds were not categorized as OAA analogues due to the different hybridization states and geometry of their terminal groups. The carbon atom in a carboxylate anion is $sp^2$-hybridized, whereas the sulfur atom can be considered essentially $sp^3$-hybridized (Reed, A. E., and Schleyer, P. V. (1990) Chemical Bonding in Hypervalent Molecules—the Dominance of Ionic Bonding and Negative Hyperconjugation over D-Orbital Participation. *J Am Chem Soc* 112, 1434-1445). The carboxylate group is planar with $C_2v$ geometry, as opposed to the nonplanar $C_3v$ geometry of the sulfonyl group (Kanyo, Z. F., and Christianson, D. W. (1991) Biological recognition of phosphate and sulfate. *J Biol Chem* 266, 4264-4268). Although the electronic charge for both groups is the same (−1), the sulfonyl group is more electron dense. The sulfonyl monocarboxylates were not categorized as PEP analogues for similar reasons: a slight change in hybridization state (the phosphorous atom in a phosphoryl group has $sp^3$ hybridization and $C_3v$ geometry), electron density, and a decrease of 1 in net electronic charge (Radzicka, A., and Wolfenden, R. (1991) Analogues of intermediates in the action of pig kidney prolidase. *Biochemistry* 30, 4160-4164). As mentioned above, β-sulfopyruvate was previously reported to be a potent reversible inhibitor of avian liver mPEPCK, with a $K_i$ value of 7 µM. The analogue was competitive with respect to OAA, with which it is isoelectronic. We have placed sulfonyl monocarboxylates in a separate class of PEPCK inhibitors, and may potentially be considered as either OAA or PEP analogues, because the sulfonyl group of these compounds does not perfectly mimic either the carboxyl or phosphoryl functionalities, and thus could potentially compete with substrates for binding at either phosphoryl- or carboxyl-binding sites. However, as demonstrated by the structure of PEPCK in complex with sulfoacetate, the sulfo-group appears, in the case of recognition by PEPCK, to be better analogue of the carboxylate group than the phosphate group.

Sulfoacetate (Compound 23) is a competitive inhibitor of PEPCK with respect to PEP, with a $K_i$ value of 83 µM (Table 3), which is similar to the $K_m$ value for PEP determined under these conditions. In contrast to the other micromolar inhibitors, sulfoacetate does not mimic the binding of OAA by coordinating directly to the active site metal, as would be predicted by the absence of cis-planar carbonyl groups. This inhibitor instead binds in a hybrid orientation, mimicking elements of both OAA and PEP recognition. The carboxylate of sulfoacetate binds in an identical orientation to the C1 carboxylate of PEP forming the same edge on interaction with Y235 and a hydrogen bond between the carboxylate and N403. In contrast, the sulfo-group does not mimic the binding of the phosphate of PEP; instead the sulfo-group is located similarly to that of the C1 carboxylate of OAA, interacting with R87 and R405 (FIG. 1F). Therefore, it is apparent that the combination of the edge on aromatic interaction and the hydrogen-bonding and electrostatic interactions with R87/405 and N403 are sufficient to result in the tight binding of the inhibitor in the absence of direct coordination to the active site manganese ion.

Figure 2A:
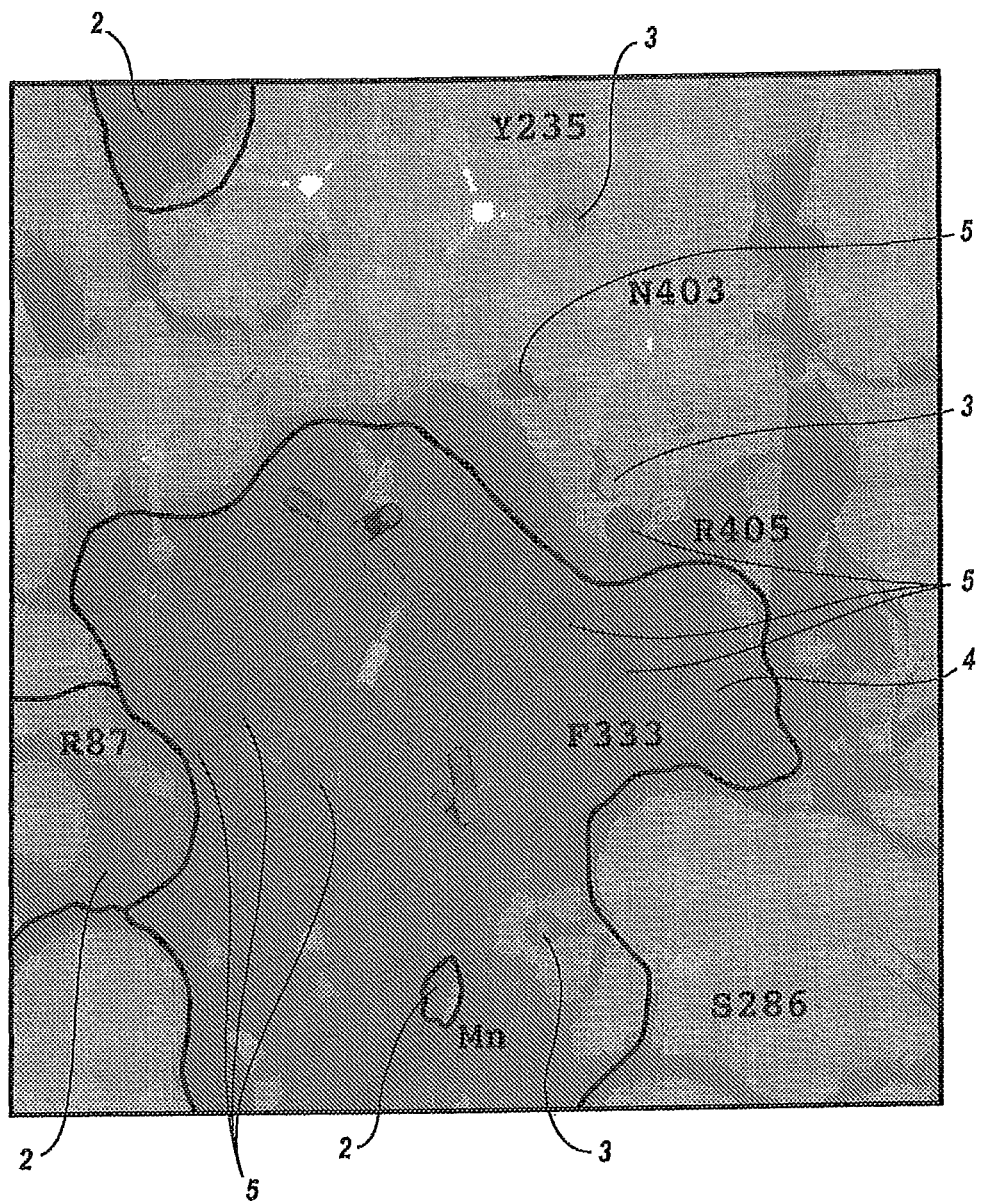
FIGS. 2A-2B show the stereoview of the OAA/PEP binding site of the lid open form of rat cPEPCK. The shading of the protein surface was generated according to the calculated electrostatic surface potential. The areas range from (2) (shading 1; −0.5V) to (4) (shading 2; +0.5V). The electrostatic surface is rendered semi-transparent illustrating the residues discussed in the text that are important for substrate recognition. These residues are labeled and rendered as ball-and-stick-models. Bound oxalate and sulfoacetate are shown as stick models demonstrating the boundaries of the OAA/PEP binding site. The active site manganese ion is labeled and rendered as a pink sphere. For clarity, the electrostatic surface was omitted for the active site manganese ion.
Figure 2B:
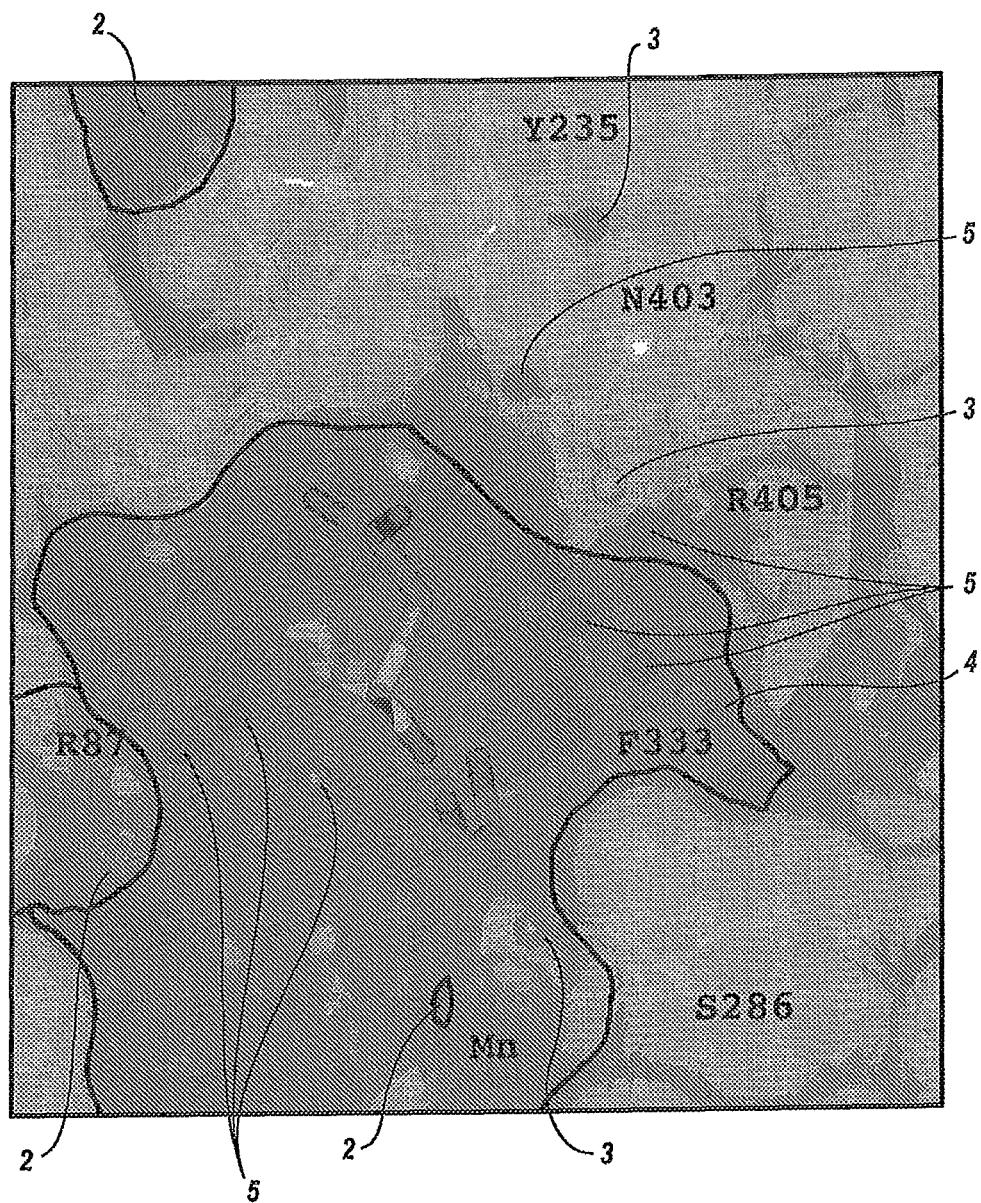

The analogue of sulfoacetate, 2,2-dimethylsulfoacetate (Compound 24), is also a competitive inhibitor, but with a $K_i$ 25-fold greater than that of sulfoacetate (Table 3). This decrease in binding affinity is presumably due to the presence of the bulky methyl groups. 3-Sulfonopropionate (Compound 25) is also a poor inhibitor (Table 3), but its amino analogue cysteic acid (Compound 26) is even less inhibitory, whereas the related compound cysteine sulfinate (Compound 27) does not cause inhibition. Sulfosuccinate (Compound 4) is a poor inhibitor, with a $K_i$ value of approximately 3.3 mM (Table 3); however, this inhibition is noteworthy considering that the parent compound succinate (Compound 3) is even less effective (Table 3). Sulfosuccinate and aspartate are both analogues of succinate, but sulfosuccinate and not aspartate (Table 1, Compound 9) inhibits; this difference is most likely due to the positive charge on aspartate and a negative charge on sulfosuccinate at the same carbon. These compounds also provide further evidence that the presence of an amino group on the carbon atom α to the terminal carboxyl group inhibits binding. No compound tested in this study runs counter to this observation (Table 1). These results are in agreement with a previous report that suggested that a change in the hybridization state of the C2 carbon of PEP from $sp^2$ to $sp^3$ or the incorporation of bulky groups at this position decreases affinity. Our structural data further support these observations, with the tight framing of the PEP binding pocket by F333 and R87 allowing for relatively few changes at this site of the molecule and the overall positive electrostatic potential at the active site of PEPCK (FIGS. 2A-2B).

It has now been found that diphosphoryls and diphosphonates can be PEPCK inhibitors. Pyrophosphate (Compound 28) is a noncompetitive inhibitor of PEPCK with respect to PEP, with a $K_i$ value of 34 µM and a $K_{ii}$ value of 63 µM. With IDP as the variable substrate, however, the inhibition pattern suggests that pyrophosphate is a competitive inhibitor ($K_i$ of 172 µM; Table 3), perhaps competing with the α- and β-phosphates of IDP. The methylene analogue of pyrophosphate, methanediphosphonate (Compound 29), is also a noncompetitive inhibitor of PEPCK with respect to PEP, with inhibition constants similar to those of pyrophosphate (Table 3). This similarity in the inhibition patterns and constants observed for pyrophosphate and methanediphosphonate suggests that both compounds may bind at the same site. Although methanediphosphonate has not been previously reported as a reversible inhibitor of PEPCK from any source, or as a reversible inhibitor of any PEP-utilizing enzyme, it has been reported to be an inhibitor of pyrophosphate-dependent phosphofructokinase, with an $IC_{50}$ of >2 mM. The homologue of methanediphosphonate, 1,2-ethanediphosphonate (Compound 30), is a poor competitive inhibitor, with a $K_i$ value of 5.1 mM (Table 3). The functional groups on 1,2-ethanediphosphonate are in the same relative positions as those of phosphoglycolate, 3-phosphonopropionate, and 3-sulfonopropionate, each of which is a moderate to poor inhibitor of the enzyme.

The corresponding sulfonate analogues of pyrophosphonate and methanediphosphonate are pyrosulfate and methanedisulfonate (Compound 31). Pyrosulfate cannot be evaluated as an inhibitor because it is instantaneously converted to sulfuric acid in an aqueous environment; however, methanedisulfonate is stable and was found, like its diphosphonate analogue, to be a noncompetitive inhibitor (Table 3). The inhibition of PEPCK by pyrophosphate was anticipated, based either on its ability to chelate divalent metal cation at the active site of the metal-dependent protein or on its mimicry of the oligophosphate side chain of the nucleotide substrate (Harris, W. R., and Nesset-Tollefson, D. (1991) Binding of phosphonate chelating agents and pyrophosphate to apo-transferrin. Biochemistry 30, 6930-6936). Thus, it can be predicted that methanediphosphonate and methanedisulfonate, being homo-bifunctional compounds of similar size and configuration as pyrophosphate, may also be non-competitive inhibitors (Table 3, Compounds 29 and 31). Given that the gamma-phosphate of GTP acts a bridging ligand between the active site and nucleotide metals, these bi-functional compounds could be blocking the gamma phosphate's interaction with the active site metal, as this site has been crystallographically observed to bind anions such as sulfate (Holyoak and Sullivan, unpublished data). It is therefore possible that these short bi-functional compounds are bridging the two metals by binding in the γ- and β-phosphate binding site, thereby inhibiting phosphoryl transfer. The competitive inhibition of pyrophosphate against IDP is consistent with this conclusion, as the pyrophosphate and IDP are competing at least partially for the same site.

Using the double inhibition approach of Janc et al., it was determined whether methanedisulfonate (noncompetitive inhibitor) and sulfoacetate (competitive inhibitor) could bind simultaneously to PEPCK. The parallel double inhibition patterns obtained with these two inhibitors (data not shown) are consistent with their binding being mutually exclusive. 1,2-Ethanedisulfonate (Compound 32), a homologue of methanedisulfonate, also inhibits, but weakly, with a $K_i$ value of approximately 3.0 mM (Table 3). The sulfonyl groups on 1,2-ethanedisulfonate are in the same relative positions as the functional groups of the previously mentioned analogues succinate, sulfosuccinate and 1,2-ethanediphosphonate. Because all of these compounds have similar structures and are poor-to-moderate inhibitors, the decrease in affinity most likely results from their inability to mimic the bound conformation of OAA, based upon the qualities previously discussed. They are, instead, predicted to bind in a fashion similar to PEP, PGA and 3-phosphonopropionate.

In general, those molecules that fail to inhibit PEPCK are predicted to be sterically prohibited from binding to the active site and/or carry positively charged functional groups incompatible with the positively charged active site (FIGS. 2A-2B). Of the molecules that demonstrate some affinity for the enzyme (Table 3), the structural data suggest that the phosphoryl- and phosphono-monocarboxylates attain the correct polarity in the active site via the phosphoryl/phosphono group, orienting the phosphorus containing moiety toward the manganese center and positioning the carboxylate towards the end of the pocket and Y235 and N403. These are weak inhibitors that in a general sense mimic the binding orientation of PEP; however, they appear to have a reduced edge-on carboxylate interaction with Y235 and lose the hydrogen bonding interaction with N403 as the result of movement toward the metal and inner-sphere coordination of the phosphate to the active site manganese ion.

Based upon the structures of PGA and 3-phosphonopropionate, we predict that 2,2-dimethylsulfoacetate, 1,2-ethanediphosphonate, and 3-sulfopropionate would bind in a similar outersphere/PEP-like conformation, resulting in their observed millimolar $K_i$ values. It appears that PEP obtains its higher affinity for the enzyme when compared to the other PEP analogues, as represented by PGA and 3-phosphonopropionate (89 μM vs 1-2 mM, Table 3), by taking advantage of aromatic interactions with Y235 and/or F333. Both PGA and 3-phosphonopropionate lack the C3 methylene group, which appears to make a favorable aromatic interaction with F333. This interaction also orients the carboxylate of PEP to favorably interact with Y235. The structural data suggest that the loss of the F333 interaction in PGA and 3-phosphonopropionate results in a general shift in the position of the bound inhibitor as it coordinates directly to the manganese ion, and as a result, the edge on aromatic-carboxylate interaction with Y235 is eliminated or at least significantly decreased.

While a priori phosphonoformate was predicted to be a PEP analogue, the structural data demonstrate that it mimics the binding of OAA. Consistent with this observation is its micromolar $K_i$ value similar to the $K_i$ of oxalate. The structural data show that in phosphonoformate the juxtaposition of the two carbonyl oxygens of the phosphonate and the carboxylate allows it to mimic the planar cis $sp^2$ central skeleton of OAA/oxalate, thus making it an effective analogue of OAA that binds directly to the manganese ion. Similar to oxalate, the additional interactions of the other phosphono and carboxylate oxygens with R87, S286, and R405 appear to result in the observed micromolar binding affinity.

Sulfoacetate is an outlier that utilizes motifs of both OAA and PEP recognition to achieve a reasonable binding affinity. Thus, while binding in a position similar to PEP that results in the edge on Y235 carboxylate interaction, the sulfo group does not mimic the outersphere coordination of the phosphate of PEP or the innersphere coordination of PGA or phosphonopropionate. Instead, the sulfo group mimics the C1 carboxylate of OAA, interacting in a similar fashion with R87 and R405.

Together the kinetic and structural data suggest the following motifs for substrate/inhibitor recognition (FIGS. 2A-2B): Cis-planar $sp^2$ carbonyl moieties facilitate the coordination of the ligand directly to the active site metal. As suggested by the binding of OAA, oxalate and phosphonoformate, (1) the terminal carbonyl can be a carboxylate in order to facilitate interaction with S286 (FIGS. 1A-1F); (2) a bridging oxygen or similar electron rich atom between the C1 carboxylate and C3 carbonyl of OAA allows for tighter binding by exploiting electrostatic and hydrogen bonding possibilities with R405; (3) carboxylate or sulfonate at the position corresponding to the C1 carboxylate of OAA exploits further interactions with R87 and R405; and (4) aromatic and hydrogen bonding interactions at a position corresponding to the C1 carboxylate of PEP and Y235 and N403 respectively appear to be responsible for at least an order of magnitude increase in binding efficiency.

At best, all of the molecules tested that are effective inhibitors (e.g., sulfoacetate, oxalate, and phosphonoformate) or substrates (e.g., PEP, OAA) appear to take advantage of only two of the possible interactions described above in order to achieve the observed micromolar $K_i$ or $K_m$ values. In theory, it should be possible to obtain quite high affinities and specificity if all four interactions are exploited, based upon the observed differences in inhibition by pyruvate and oxalate discussed previously. In addition, the binding of sulfoacetate suggests that larger molecules based upon the structure of OAA that could extend in the active site and form the favorable interactions with Y235, F333 and N403 would be potent and selective PEPCK inhibitors.

In conclusion, this study provides the first structure-function analysis of the PEP/OAA binding site of mammalian PEPCK and illustrates the mechanism of substrate/inhibitor molecular recognition utilized by PEPCK, which can be exploited in the design of effective and selective inhibitors of PEPCK. A summary of the figures is provided below.

Figure 1B:
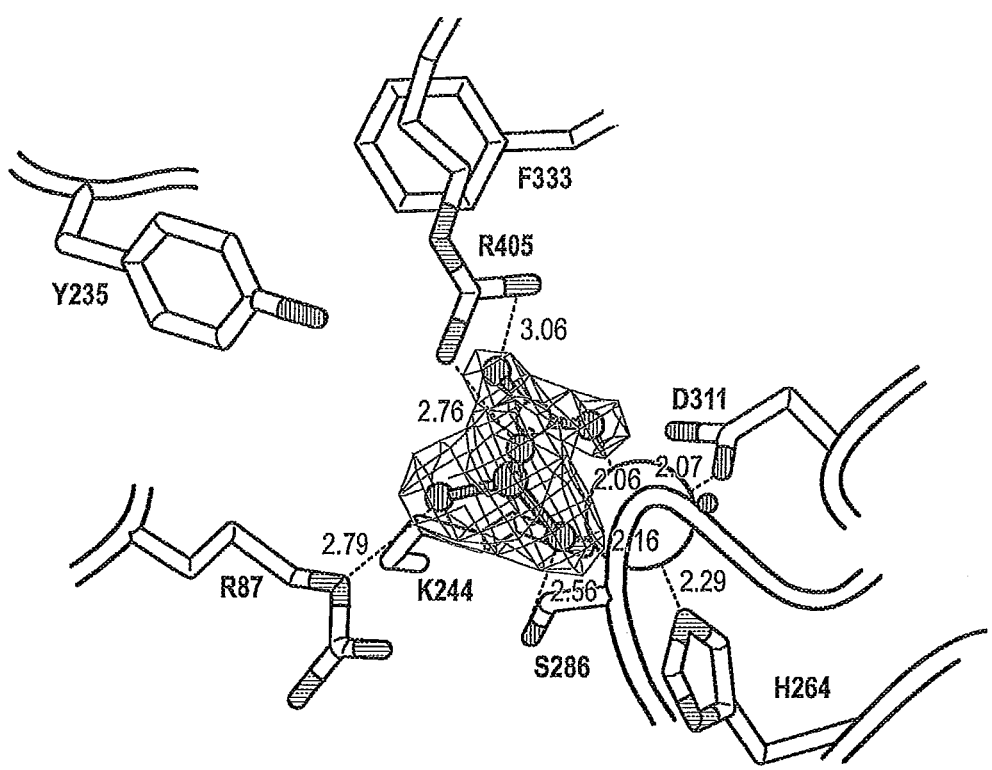
Figure 1C:
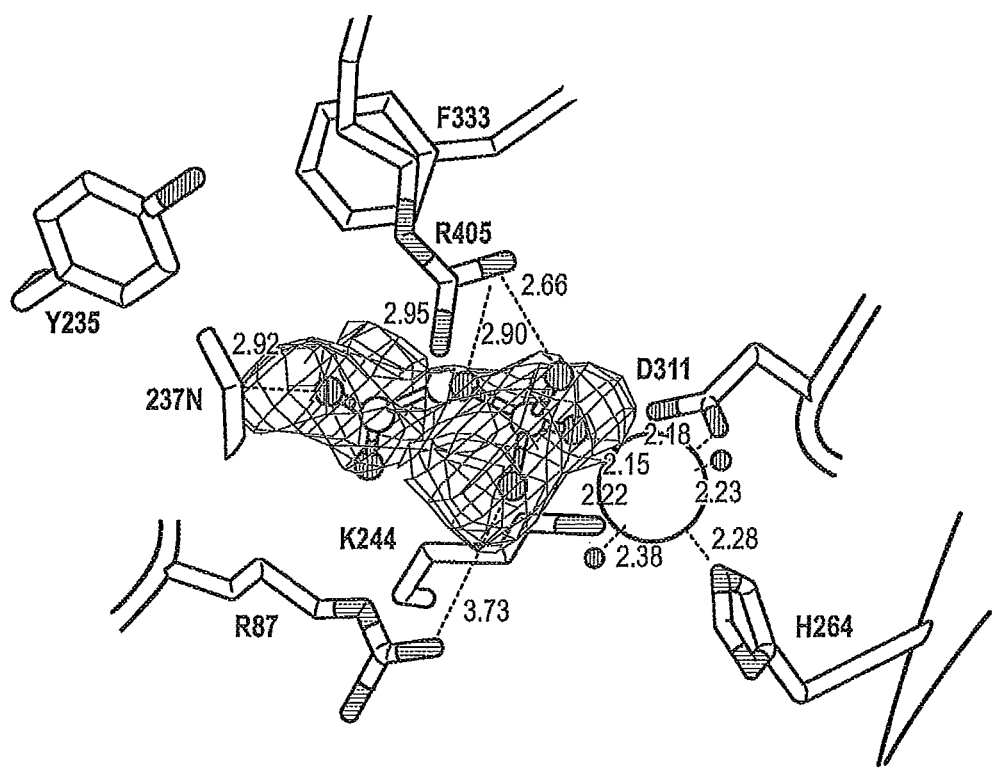
Figure 1D:
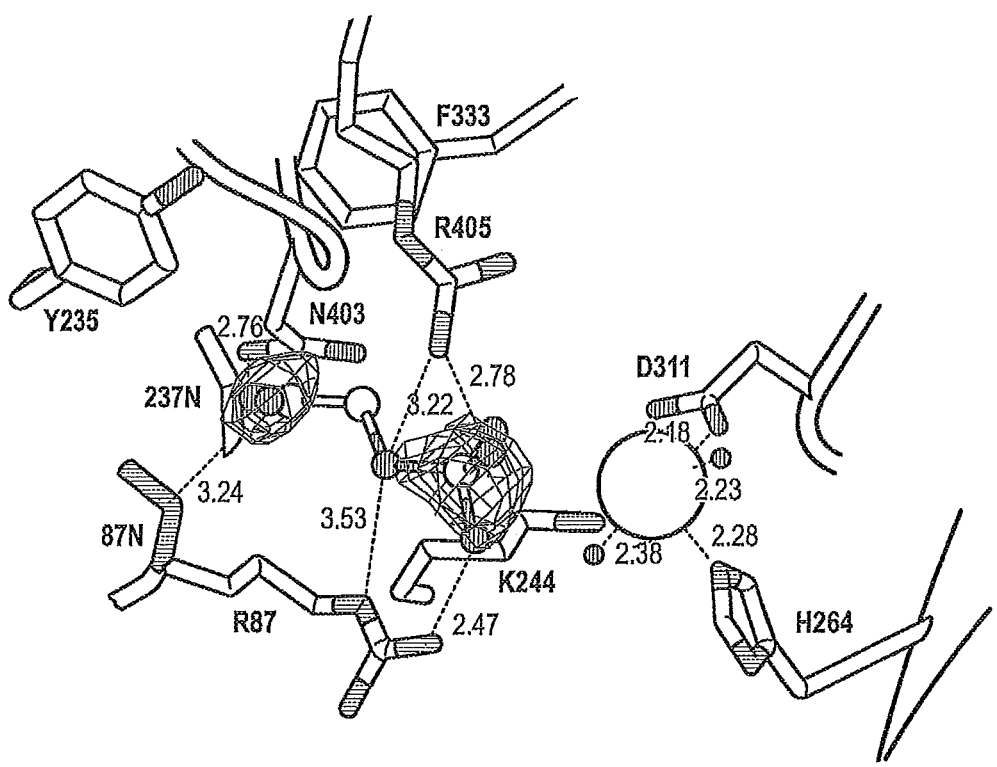
Figure 1E:
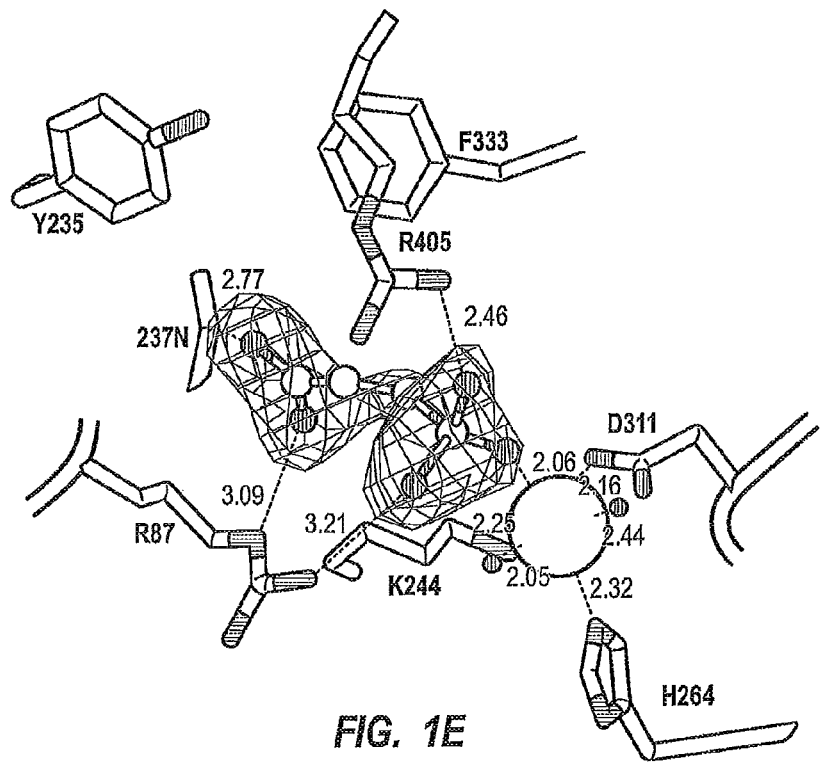
Figure 1F:
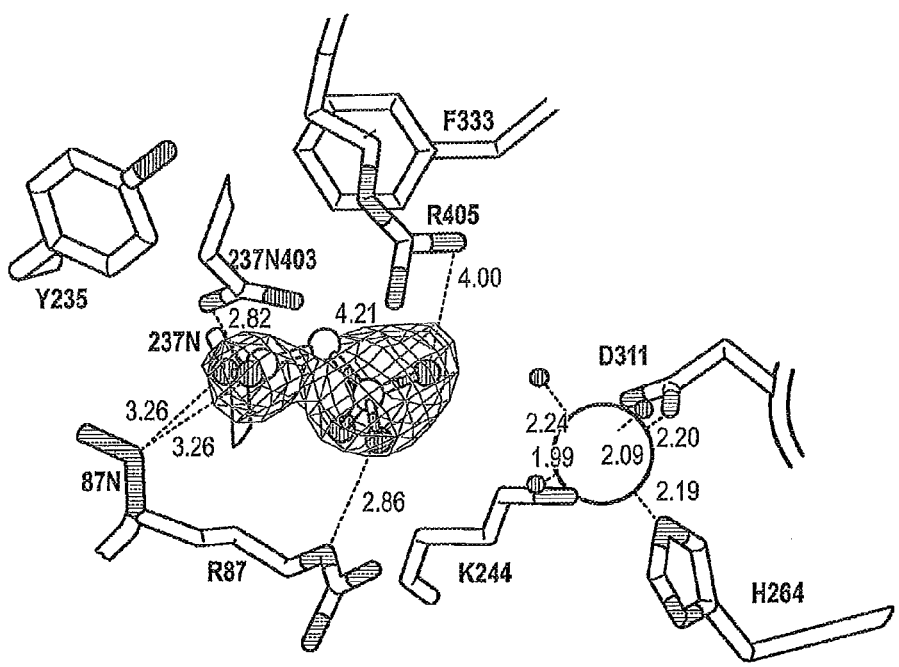

FIG. 1A shows the interaction of oxalate at the PEPCK active site. The bicarboxylate structure is specifically recognized by direct coordination of two of the carboxylate oxygens through direct coordination to the active site manganese ion (2.16 and 2.31 Å respectively) as well as hydrogen bonding of one of the oxygens to serine 286 (S286). The other carboxylate oxygens form discrete hydrogen bonds with R405 and R87 (2.93, 3.06 and 2.78 Å).

FIG. 1B shows the interaction of phosphonoformate at the PEPCK active site. The C1 carboxylate interacts in an identical fashion with the enzyme as the similar carboxylate in oxalate shown in FIG. 1A. Two of the oxygens of the phosphono group are able to make similar interactions with S286 and R87 however the later interactions occurs through the NE of R87 rather than the terminal amino group as observed in the oxalate complex.

FIGS. 1C and 1D show the two binding orientations for phosphoglycolate (PGA) observed at the active site of PEPCK. PGA is observed to bind in two different orientations. In C) one phosphoryl oxygen is observed to coordinate directly to the active site manganese ion (2.15 Å) in a similar fashion to the C1 carboxylate of phosphonoformate and oxalate in panels A and B. In the conformation shown in D, PGA adopts the same outer-sphere conformation with the active site manganese ion as seen with the substrate PEP indirectly interacting with the metal ion through two water molecules coordinated to the metal ion. In both orientations the other phosphoryl oxygen atoms make favorable interactions with the guanidinium groups of R87 and R405 however as depicted the specific contacts difference between the two conformers. In both orientations, the C2 carboxylate extends away from the manganese ion towards the back of the binding pocket making discrete interactions with the backbone nitrogen of residue 237 as well as the backbone nitrogen of R87 and the side chain of asparagine 403(N403) in the case of the conformation observed in D). In both orientations the side chain of tyrosine 235 (Y235) is observed in its rearward conformation and the C2 carboxylate makes a favorable edge on carboxylate-aromatic interaction.

FIG. 1E shows the interaction of phosphonopropionate at the PEPCK active site. Phosphononopropionate interacts in an identical conformation to that observed in panel C for PGA. The lack of the second binding conformation is due to the absence of the bridging oxygen in phosphonopropionate that makes the favorable interaction (3.22 Å) with the amino group of R405 in panel D. Further the lack of the bridging oxygen prevents the molecule from adopting an additional conformation that occurs upon the formation of the PGA-GDP nucleotide complex (Sullivan and Holyoak, 2008) resulting in less dynamic motion in the inhibitor as the lack of the bridging oxygen in phosphonopropionate precludes this additional conformation in the presence of GDP nucleotide (unpublished data).

FIG. 1F shows the interaction of sulfoacetate at the PEPCK active site. Unlike the other inhibitors, sulfoacetate is observed to occupy only the rearward pocket of the PEPCK active site with no interaction with the active site manganese ion. The C2 carboxylate interacts with the enzyme in an identical fashion to the PGA conformation shown in panel D while the C1 sulfate group occupies the CO2 binding site of the substrate OAA (Sullivan and Holyoak, 2007) through hydrogen bonding interactions with R87 and a salt bridge with R405.

FIGS. 2A-2B show bound oxalate and sulfoacetate are shown as stick models demonstrating the boundaries of the OAA/PEP binding site. The portions labeled by (2) correlates to a negative charge, and elements identified by (3) are negatively charged. The portions labeled with (4) correlates to a positive charge, and elements identified by (5) are positively charged. The non-overlapping nature of the two inhibitors defines the two subsites in the OAA/PEP binding site of the PEPCK active site. All of the residues that can directly interact with an inhibitor molecule that occupies both of these subsites simultaneously are shown and labeled. Connection of these two individual subsites in a single molecular scaffold will lead to potent and selective inhibitors of PEPCK as anti-hyperglycemic agents.

Figure 3:
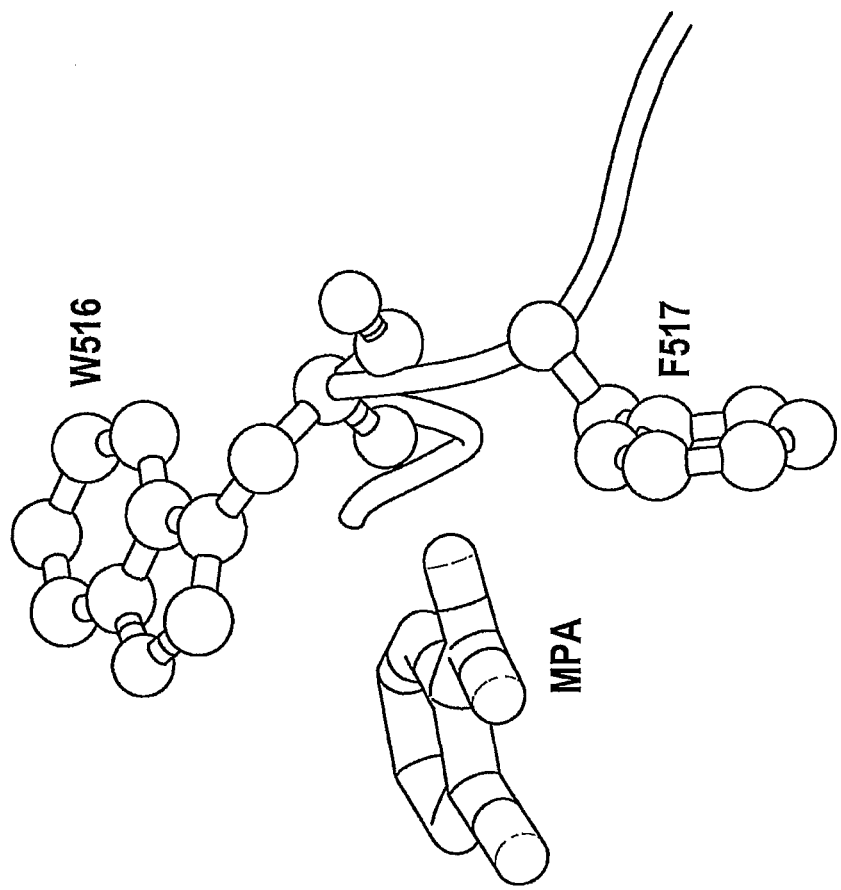
FIG. 3 is a schematic representation of an allosteric binding site for 3-mercaptopicolinic acid (MPA) based upon crystallographic studies of cytosolic PEPCK. The active site of PEPCK is indicated by the active site manganese ion (sphere). The allosteric site is illustrated by the bound position of MPA framed by the P-loop domain and the 514-533 loop. W516 and C288 are involved in MPA binding. The F517 residue that changes conformation upon binding to the allosteric site is shown.
Figure 3:
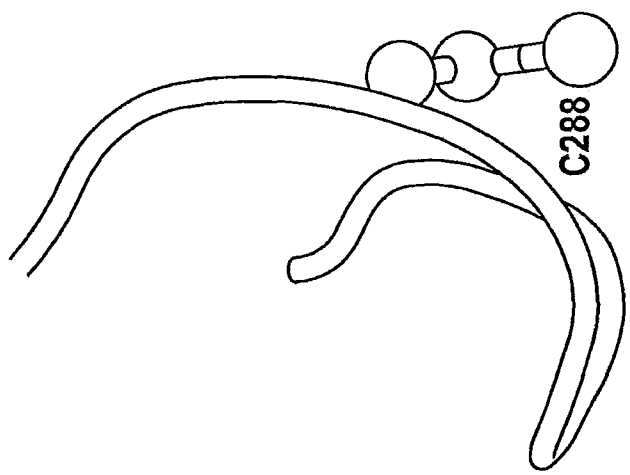

FIG. 3 shows a novel allosteric binding site for regulation of PEPCK activity, such as PEPCK inhibition. Crystallographic studies of cytosolic PEPCK illustrate that a novel binding site for the molecule 3-mercaptopicolinic acid (MPA) exists in a unique pocket adjacent to the active site of PEPCK. This site is framed by the active site P-loop and the loop composed of residues 514-533 (FIG. 3). Kinetic data demonstrate that MPA binds to this site and is competitive with nucleotide binding with an apparent affinity of ~100 µM. Analysis of the crystallographic data from several complexes of PEPCK with MPA and various substrates and substrate analogues illustrates that binding to this allosteric site results in a conformational change involving residue F517 and more generally an alteration in the position of 514-533 loop. These conformational changes distort the nucleotide-binding pocket and preclude the binding of nucleotide to PEPCK resulting in catalytic inhibition. While the inhibition of PEPCK by MPA has been previously described, this work is the first to identify the novel allosteric binding site and describe the allosteric mechanism of inhibition by this compound. Knowledge of this binding site can now be utilized to guide the design of molecules with a high affinity for this binding site in the development of anti-hyperglycemic agents targeting PEPCK in the treatment of diabetes-associated hyperglycemia.

Figure 5:
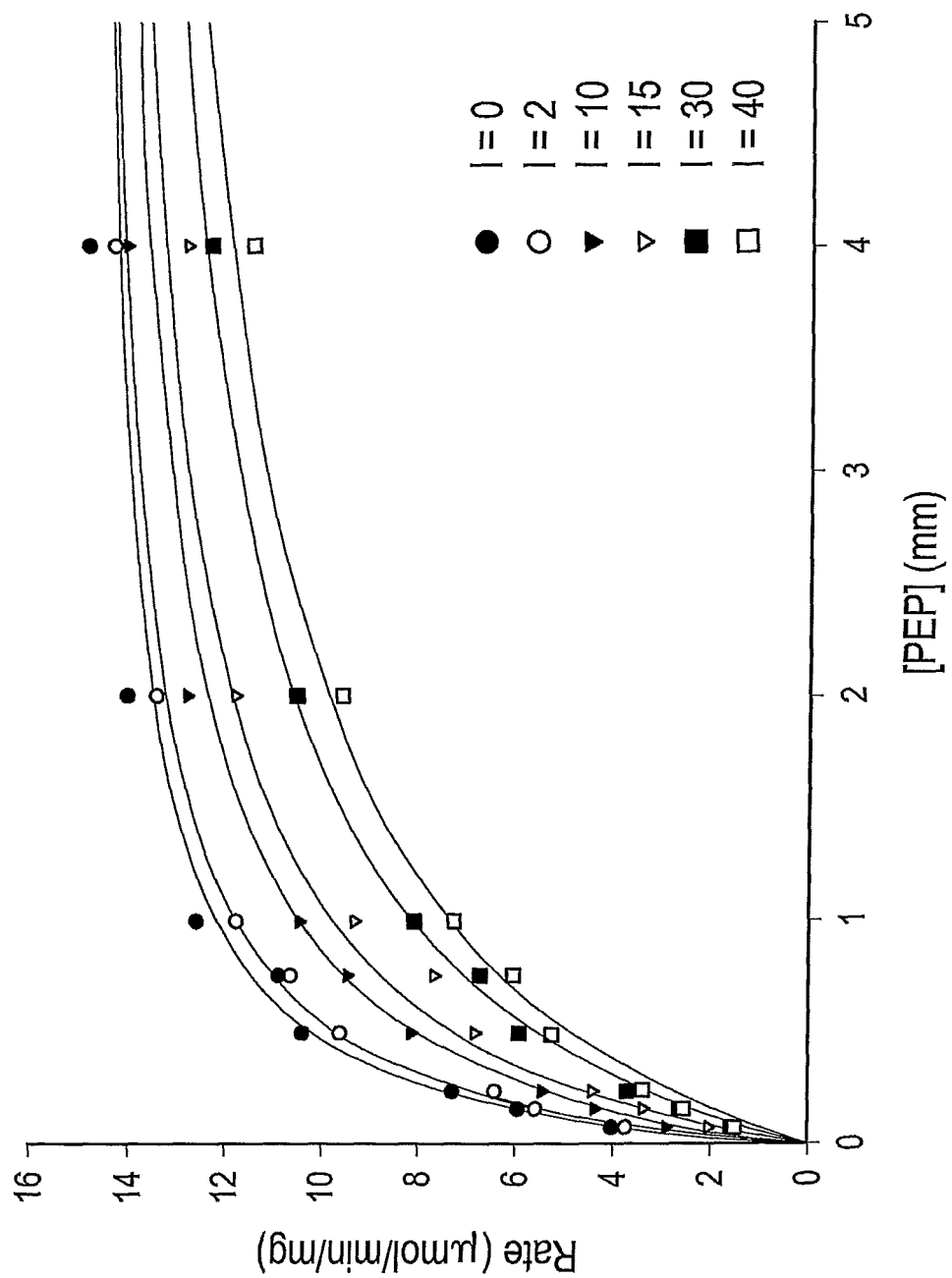
FIG. 5 includes a graph that illustrates the inhibition data for CMMP against PEPCK, where the data illustrates the inhibition of PEPCK by CMMP and demonstrate that it is competitive in its binding with PEP. The global fit of the data to a' competitive inhibition model gives a Ki value of 12 uM. The 'I' values given in the legend are the concentrations of CMMP used in uM.

FIG. 4 shows that CMMP (e.g., Formula C) is an effective PEPCK inhibitor. Due to the partially overlapping binding sites for PEP and OAA prior to lid closure, obtaining both selectivity and potency in active site inhibitors should be possible because of the unique sub-sites existing within the PEP/OAA binding site due to the dynamic structural changes induced by lid opening and closing. This was originally supported by the inhibition of PEPCK by sulfoacetate. In that work we demonstrated that sulfoacetate obtains a reasonable level of inhibition ($K_i$=82 µM) by bridging the two active site sub-sites and exploiting interactions utilized in the binding of both OAA and PEP. Based upon that work, we proposed a novel scaffold to be utilized in the development of molecules that bridge these two sub-sites with and in doing so would gain potency and, perhaps more importantly with a metabolic enzyme like PEPCK, specificity. This scaffold is Formulas C, E, and/or G and an example is CMMP. Kinetic analysis demonstrates that CMMP is a competitive inhibitor against PEP in the PEPCK reaction. It exhibits a reasonable $K_i$ (12 µM) and the crystal structure of the PEPCK-CMMP complex illustrates that the molecule binds exactly as predicted by our previous studies, bridging the OAA and PEP sub-sites (FIG. 4). This molecule thereby gains both potency and specificity for PEPCK. FIG. 5 shows the inhibition data for CMMP against PEPCK, where the data illustrates the inhibition of PEPCK by CMMP and demonstrate that it is competitive in its binding with PEP. The information obtained from FIGS. 4 and 5 indicate that derivatives of CMMP, as shown by the scaffolds of Formulas E and G, are likely to be similarly effective as CMMP.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference (Sullivan, S. M. and Holyoak, T. Enzymes with lid-gated active sites must operate by an induced fit mechanism instead of conformational selection. Proc Natl Acad Sci USA 2008; 105:13829-34; Sullivan, S. M. and Holyoak, T. Structures of rat cytosolic PEPCK: Insight into the mechanism of phosphorylation and decarboxylation of oxaloacetic acid. Biochemistry 2007; 46:10078-88).

TABLES

TABLE 1

Substrate Analogues of Rat Liver Cytosolic Phosphoenolpyruvate Carboxykinase.

| # | Name | Chemical Formula | % Activity Remaining[a] |
|---|---|---|---|
| | Dicarboxylates | | |
| 1 | Oxalate[b] | $CO_2^-CO_2^-$ | 11[c] |
| 2 | Malonate[b] | $CO_2^-CH_2 CO_2^-$ | 102[c] |
| 3 | Succinate[b] | $CO_2^-CH_2CH_2 CO_2^-$ | 91[c] |
| 4 | Sulfosuccinate[d] | $CO_2^-CH(SO_3^-)CH_2 CO_2^-$ | 55[c] |
| 5 | Maleate | $CO_2^-CH: CH\, CO_2^-$ (cis) | 52[e] |
| 6 | Fumarate | $CO_2^-CH: CH\, CO_2^-$ (trans) | 83[e] |
| 7 | Itaconate | $CO_2^-CH_2C(:CH_2) CO_2^-$ | 91[c] |
| 8 | 1,2-Cyclopentanedicarboxylate | $CO_2^-CH(CH_2)_3CH\, CO_2^-$ | 91[c] |
| 9 | L-Aspartate[b,d] | $CO_2^-CH_2CH(NH_3^+) CO_2^-$ | 112[c] |
| | Phosphonyl/phosphoryl monocarboxylates | | |
| 10 | Phosphonoformate[b] | $PO_3^{2-}CO^{2-}$ | 12[c] |
| 11 | Phosphonoacetate[b] | $PO_3^{2-}CH_2 CO^{2-}$ | 108[c] |

TABLE 1-continued

Substrate Analogues of Rat Liver Cytosolic Phosphoenolpyruvate Carboxykinase.

| # | Name | Chemical Formula | % Activity Remaining[a] |
|---|---|---|---|
| 12 | 3-phosphonopropionate | $PO_3H^-CH_2CH_2 CO^{2-}$ | 57[c] |
| 13 | Phosphoglycolate[b] | $PO_3^{2-}OCH_2 CO^{2-}$ | 25[c] |
| 14 | 2-D-Phosphoglycerate[b,d] | $PO_3^{2-}OCH(CH_2OH)\, CO^{2-}$ | 110[c] |
| 15 | 2-(Phosphonomethyl)acrylate[b] | $PO_3H^-CH_2C(:CH_2)\, CO^{2-}$ | 92[c] |
| 16 | 6-phosphogluconate[b] | $PO_3^{2-}OCH_2(CHOH)_4 CO^{2-}$ | 117[c] |
| 17 | N-Phosphonomethylglycine[b] | $PO_3H^-CH_2NHCH_2 CO^{2-}$ | 104[c] |
| 18 | 2-Amino-3-phosphonopropionate[d] | $PO_3H^-\, CH_2CH(NH_3^+)\, (CO^{2-})$ | 94[c] |
| 19 | 2-Amino-4-phosphonobutyrate[b] | $PO_3H^-(CH_2)_2CH(NH_3^+)\, (CO^{2-})$ | 104[c] |
| 20 | 2-Amino-5-phosphonovalerate[d] | $PO_3H^-(CH_2)_3CH(NH_3^+)\, CO^{2-}$ | 98[f] |
| 21 | Serine phosphate[d] | $PO_3^{2-}OCH_2CH(NH_3^+)\, CO^{2-}$ | 108[f] |
| 22 | Threonine phosphate[d] | $PO_3^{2-}OCH(CH_3)CH(NH_3^+)\, CO^{2-}$ | 97[c] |
| | Sulfonyl/sulfinyl monocarboxylates | | |
| 23 | Sulfoacetate | $SO_3^-CH_2 CO^{2-}$ | 18[f] |
| 24 | 2,2-Dimethylsulfoacetate | $SO_3^-C(CH_3)_2 CO^{2-}$ | 65[c] |
| 25 | 3-Sulfopropionate | $SO_3^-CH_2CH_2 CO^{2-}$ | 69[c] |
| 26 | Cysteic acid[d] | $SO_3^-CH_2CH(NH_3^+)\, CO^{2-}$ | 76[c] |
| 27 | Cysteine sulfinic acid[d] | $SO_2^-CH_2CH(NH_3^+)\, CO^{2-}$ | 105[c] |
| | Diphosphoryls | | |
| 28 | Pyrophosphate[b] | $PO_3H^-O\, PO_3H^-$ | 22[f] |
| 29 | Methanediphosphonate | $PO_3H^-CH_2\, PO_3H^-$ | 4[f] |
| 30 | 1,2-Ethanediphosphonate | $PO_3H^-CH_2CH_2\, PO_3H^-$ | 96[e] |
| | Disulfonates | | |
| 31 | Methanedisulfonate | $SO_3^-CH_2\, SO_3^-$ | 4[f] |
| 32 | 1,2-Ethanedisulfonate | $SO_3^-CH_2CH_2\, SO_3^-$ | 42[e] |
| | Epoxy/aromatic compounds | | |
| 33 | Phosphomycin | $CH_3CH[O]CHPO_3^{2-}$ | 108[c] |
| 34 | Phenylphosphate | $C_6H_5OPO_3^{2-}$ | 96[c] |
| 35 | p-Nitrophenylphosphate | $NO_2C_6H_4OPO_3^{2-}$ | 103[c] |

[a]In this preliminary screen, the inhibition by each compound was tested twice using two different preparations of PEPCK. The remaining percent activity listed below represents the average of the two values.
[b]These compounds have been previously evaluated as either reversible inhibitors or alternative substrates for rat liver cytosolic PEPCK and other PEP-utilizing enzymes (see text for references).
[c]Activity was determined at analogue and PEP concentrations of 3 mM and 40 µM, respectively.
[d]For the analogues containing a chiral center, the chiral carbon is italicized.
[e]Activity was determined at analogue and PEP concentrations of 6 mM and 40 µM, respectively.
[f]Activity was determined at analogue and PEP concentrations of 1.5 mM and 40 µM, respectively.

TABLE 2

Data and Model Statistics for the PEPCK-$Mn^{2+}$-oxalate, PEPCK-$Mn^{2+}$-phophonoformate, PEPCK-$Mn^{2+}$-PGA, PEPCK-$Mn^{2+}$-phosphonopropionate and PEPCK-$Mn^{2+}$-sulfoacetate complexes[a].

| | PEPCK-$Mn^{2+}$-oxalate | PEPCK-$Mn^{2+}$-phosphono-formate | PEPCK-$Mn^{2+}$-PGA | PEPCK-$Mn^{2+}$-phosphono-propionate | PEPCK-$Mn^{2+}$-sulfo-acetate |
|---|---|---|---|---|---|
| wavelength (Å) | 1.54 | 1.54 | 1.54 | 1.54 | 1.54 |
| space group | $P2_1$ | $P2_1$ | $P2_1$ | $P2_1$ | $P2_1$ |
| unit cell | a = 64.0 Å b = 118.9 Å | a = 62.3 Å b = 119.5 Å | a = 60.7 Å b = 119.7 Å | a = 45.3 Å b = 119.4 Å | a = 45.2 Å b = 119.0 Å |

TABLE 2-continued

Data and Model Statistics for the PEPCK-$Mn^{2+}$-oxalate,
PEPCK-$Mn^{2+}$-phophonoformate, PEPCK-$Mn^{2+}$-PGA, PEPCK-$Mn^{2+}$-phosphonopropionate
and PEPCK-$Mn^{2+}$-sulfoacetate complexes[a].

| | PEPCK-$Mn^{2+}$-oxalate | PEPCK-$Mn^{2+}$-phosphono-formate | PEPCK-$Mn^{2+}$-PGA | PEPCK-$Mn^{2+}$-phosphono-propionate | PEPCK-$Mn^{2+}$-sulfo-acetate |
|---|---|---|---|---|---|
| | c = 86.5 Å | c = 86.9 Å | c = 90.9 Å | c = 60.8 Å | c = 60.9 Å |
| | $\alpha = \gamma = 90.0°$ | $\alpha = \gamma = 90°$ | $\alpha = \gamma = 90°$ | $\alpha = \gamma = 90°$ | $\alpha = \gamma = 90°$ |
| | $\beta = 107.0°$ | $\beta = 107.1°$ | $\beta = 108.9°$ | $\beta = 108.7°$ | $\beta = 108.8°$ |
| resolution limit (Å) | 30.8-1.9 | 30.1-2.00 | 29.9-1.95 | 34.0-1.9 | 29.1-1.8 |
| no. of unique reflections | 91629 | 76020 | 81978 | 44417 | 50438 |
| Completeness[b] (%; all data) | 99.1 (93.6) | 98.2 (91.1) | 96.4 (93.0) | 97.1 (81.3) | 94.4 (64.9) |
| redundancy[b] | 5.5 (4.7) | 5.7 (4.5) | 6.8 (6.3) | 7.0 (5.5) | 8.5 (3.7) |
| $I/\sigma_{(I)}$[b] | 11.9 (2.1) | 9.7 (1.9) | 16.1 (2.6) | 20.2 (2.4) | 19.5 (1.7) |
| $R_{merge}$[b,c] | 0.09 (0.52) | 0.10 (0.52) | 0.07 (0.53) | 0.07 (0.53) | 0.08 (0.45) |
| no. of ASU molecules | 2 | 2 | 2 | 1 | 1 |
| solvent content (%) | 40.1 | 39.1 | 38.4 | 39.9 | 39.9 |
| $R_{free}$[b,d] (%) | 25.6 (35.2) | 24.9 (34.5) | 22.2 (33.3) | 23.3 (36.2) | 24.9 (36.8) |
| $R_{work}$[b,e] (%) | 20.7 (28.3) | 19.8 (27.2) | 18.5 (25.4) | 18.9 (30.4) | 20.5 (34.7) |
| average B values[f] protein | 10.9 | 18.1 | 18.4 | 14.1 | 12.1 |
| water | 25.1 | 31.1 | 26.7 | 28.4 | 22.9 |
| inhibitor | Oxalate Mol A 18.0 Mol B 18.6 | Phosphono-formate Mol A 16.4 Mol B 25.0 | PGA Mol A $PGA_1 = 15.7$, oc = 0.5 $PGA_2 = 22.1$, oc = 0.5 Mol B $PGA_1 = 14.4$, oc = 0.5 $PGA_2 = 19.7$, oc = 0.5 | Phosphono-propionate 19.4 | Sulfo-acetate 18.5 |
| estimated coordinate error based on maximum likelihood (Å) | 0.125 | 0.143 | 0.115 | 0.122 | 0.118 |
| bond angle rmsd (deg) | 1.119 | 1.117 | 1.125 | 1.112 | 1.237 |
| Ramachandran statistics (most favored, additionally allowed, generously allowed, disallowed) (%) | 90.5 8.7 0.6 0.2 | 90.8 8.6 0.3 0.3 | 91.2 8.2 0.6 0 | 91.0 8.2 0.8 0 | 91.4 7.8 0.8 0 |

[a]Mol A; molecule A of the crystallographic dimer
Mol B; molecule B of the crystallographic dimer
oc; ligand occupancy
$PGA_1$ and $PGA_2$ correspond to the two alternate conformations of PGA present in each molecule of the PEPCK-$Mn^{2+}$-PGA crystallographic dimer.
[b]Values in parentheses represent statistics for data in the highest-resolution shells. The highest-resolution shell comprises data in the range of 1.97-1.90, 2.07-2.00, 2.02-1.95, 1.97-1.90, and 1.85-1.80 Å for the PEPCK-$Mn^{2+}$-oxalate, PEPCK-$Mn^{2+}$-phosphonoformate, PEPCK-$Mn^{2+}$-PGA, PEPCK-$Mn^{2+}$-phosphonopropionate, and PEPCK-$Mn^{2+}$-sulfoacetate data sets, respectively.
[c]$R_{merge} = \Sigma |I_{obs} - I_{avg}| / \Sigma I_{obs}$
[d]See Brunger (36) for a description of $R_{free}$.
[e]$R_{work} = \Sigma ||F_{obs}| - |F_{calc}|| / \Sigma |F_{obs}|$
[f]B values indicated are residual B values after TLS refinement.

TABLE 3

Inhibition Constant for PEP and OAA Analogues.

| Analogue | $K_i$ | Pattern of Inhibition |
|---|---|---|
| Oxalate (1) | 89 ± 4 μM[a] | Competitive |
| Succinate (3) | >8.0 mM[b] | n.d.[c] |
| Maleate (5) | 2.0 mM[b] | n.d.[c] |
| Phosphonoformate (10) | 230 ± 14 μM[a] | Competitive |
| Phosphoglycolate (13) | 1.0 ± 0.04 mM[a] | Competitive |
| 3-Phosphonopropionate (12) | 1.9 ± 0.4 mM[a] | Competitive |
| 1,2-Ethanediphosphonate (30) | 5.1 ± 0.5 mM[a] | Competitive |
| Sulfoacetate (23) | 82.5 ± 5 μM[a] | Competitive |
| 2,2-Dimethylsulfoacetate (24) | 2.1 ± 0.2 mM[a] | Competitive |
| 3-Sulfopropionate (25) | 3.4 ± 0.3 mM[a] | Competitive |
| Sulfosuccinate (4) | 3.3 mM[b] | n.d.[c] |
| 1,2-Ethanedisulfonate (32) | 3.0 mM[b] | n.d.[c] |
| Pyrophosphate (28) | 34 ± 5 μM[a,d]<br>64 ± 7 μM[e]<br>172 ± 29 μM | Noncompetitive[f]<br>Competitive[g] |
| Methanediphosphonate (29) | 32 ± 2 μM[a,d]<br>90 ± 5 μM[e] | Noncompetitive |
| Methanedisulfonate (31) | 27 ± 3 μM[a,d]<br>168 ± 25 μM[e] | Noncompetitive |

[a]The $K_i$ values were obtained using the Cleland kinetics program for competitive or noncompetitive inhibitors.
[b]The $K_i$ values were obtained from Dixon plots using two PEP concentrations.
[c]Not determined
[d]Slope effect
[e]Intercept effect
[f]PEP was the varied substrate.
[g]IDP was the varied substrate.

What is claimed is:

1. A composition comprising an oxalate and phosphoenolpyruvate binding pocket of cytosolic phosphoenolpyruvate carboxykinase (PEPCK) in crystalline form, wherein said oxalate and phosphoenolpyruvate binding pocket comprises R87, Y235, G237, K244, S286, F333, N403 and R405 of PEPCK, and wherein the crystalline form comprises crystals that belong to space group $P2_1$ with a combination of unit cell parameters selected from the group of a=64.0 Å, b=118.9 Å, c=86.5 Å, α=γ=90° and β=107°,
a=62.3 Å, b=119.5 Å, c=86.9 Å, α=γ=90° and β=107.1°,
a=60.7 Å, b=119.7 Å, c=90.9 Å, α=γ=90° and β=108.9°,
a=45.3 Å, b=119.4 Å, c=60.8 Å, α=γ=90° and β=108.7°, and
a=45.2 Å, b=119.0 Å, c=60.9 Å, α=γ=90° and β=108.8°.

* * * * *